United States Patent
Shimagaki et al.

(10) Patent No.: US 8,584,869 B2
(45) Date of Patent: Nov. 19, 2013

(54) ABSORBENT AND COLUMN FOR EXTRACORPOREAL CIRCULATION

(75) Inventors: Masaaki Shimagaki, Shiga (JP); Yasufumi Yamamura, Shiga (JP); Katsuhisa Sato, Pueblo, CO (US); Kazuo Teramoto, Shiga (JP); Takeshige Oozeki, Shiga (JP); Shigehisa Wada, Shiga (JP)

(73) Assignee: Toray Industries, Inc., Tokyo (JP)

( * ) Notice: Subject to any disclaimer, the term of this patent is extended or adjusted under 35 U.S.C. 154(b) by 472 days.

(21) Appl. No.: 11/887,388

(22) PCT Filed: Mar. 31, 2006

(86) PCT No.: PCT/JP2006/306944
§ 371 (c)(1),
(2), (4) Date: Mar. 5, 2008

(87) PCT Pub. No.: WO2006/106972
PCT Pub. Date: Oct. 12, 2006

(65) Prior Publication Data
US 2009/0275874 A1    Nov. 5, 2009

(30) Foreign Application Priority Data

Mar. 31, 2005 (JP) .................. 2005-101466
Apr. 8, 2005 (JP) .................. 2005-111651
Apr. 8, 2005 (JP) .................. 2005-111652

(51) Int. Cl.
| | | |
|---|---|---|
| *B01D 15/38* | (2006.01) | |
| *B01D 39/00* | (2006.01) | |
| *B01D 69/08* | (2006.01) | |
| *B01D 63/00* | (2006.01) | |

(52) U.S. Cl.
USPC ...... 210/490; 210/483; 210/491; 210/500.23; 210/500.27; 210/502.1; 210/503; 210/504; 210/505; 210/506; 530/412; 530/413; 530/415

(58) Field of Classification Search
USPC ............ 210/483, 488, 489, 490, 491, 500.23, 210/500.27, 502.1, 503, 504, 505, 506, 507
See application file for complete search history.

(56) References Cited

U.S. PATENT DOCUMENTS

| | | | |
|---|---|---|---|
| 4,701,267 A | 10/1987 | Watanabe et al. | 210/806 |
| 5,407,581 A * | 4/1995 | Onodera et al. | 210/654 |
| 6,461,517 B1 | 10/2002 | Miwa et al. | 210/690 |

FOREIGN PATENT DOCUMENTS

| | | |
|---|---|---|
| EP | 0 397 403 A1 | 11/1990 |
| EP | 0 723 794 A1 | 7/1996 |
| EP | 1 579 838 A1 | 9/2005 |
| JP | 60-193468 A | 10/1985 |
| JP | 5-168706 A | 7/1993 |
| JP | 06-000220 | 1/1994 |
| JP | 6-7429 A | 1/1994 |
| JP | 6-142196 A | 5/1994 |
| JP | 10-225515 A | 8/1998 |
| JP | 2000-237585 A | 9/2000 |
| JP | 2002-035118 | 2/2002 |
| JP | 2002-113097 A | 4/2002 |
| JP | 2002-172163 A | 6/2002 |
| JP | 2003-111834 A | 4/2003 |
| JP | 2003-310751 A | 11/2003 |
| JP | 2003-339854 A | 12/2003 |
| JP | 2004-248950 A | 9/2004 |
| WO | WO2004/052270 A1 | 6/2004 |

OTHER PUBLICATIONS

Canadian Office Action dated Aug. 9, 2011, issued in Canadian Patent Application No. 2,603,073.
European Search Report dated Aug. 30, 2012, issued in European Patent Application No. 06730892.4-2320 / 1886704.

* cited by examiner

*Primary Examiner* — John Kim
(74) *Attorney, Agent, or Firm* — Kubovcik & Kubovcik

(57) ABSTRACT

The present invention provides an absorbent which can remove cells present in blood including activated leukocytes such as granulocytes and monocytes, and cancer cells as well as can remove cytokines which facilitate the activation of the remaining cells, and further has no concern for pressure loss and has high configuration stability. That is, the present invention provides an absorbent which absorbs the granulocytes and the monocytes in blood, an absorbent for cancer therapy which absorbs an immunosuppressive protein and an absorbent having a bilayer structure of a net and a nonwoven fabric, having a zeta potential of −20 mV or more, as well as a blood circulation column containing any of the absorbents filled therein.

17 Claims, No Drawings

ABSORBENT AND COLUMN FOR EXTRACORPOREAL CIRCULATION

This application is a 371 of international application PCT/JP2006/306944 filed Mar. 31, 2006, which claims priority based on Japanese patent application Nos. 2005-101466 filed Mar. 31, 2005, 2005-111651 filed Apr. 8, 2005, and 2005-111652 filed Apr. 8, 2005, each of which is incorporated herein by reference.

TECHNICAL FIELD

The present invention relates to an absorbent and a column for extracorporeal circulation, and more particularly relates to an absorbent which can efficiently remove leukocytes, inflammatory and immunosuppressive cytokines, and humoral factors from blood and is used suitably for so-called leukapheresis therapy, immunostimulatory therapy and cancer therapy, and a column for processing the blood such as a column for extracorporeal circulation utilizing the absorbent.

BACKGROUND ART

Blood contains a variety of components such as blood cells, cytokines and other humoral factors. These blood components play important roles on regulating immunity balance in a living body.

Endotoxin typified by lipopolysaccharide is a factor which exhibits a variety of biological activities involved in fever, blood pressure decrease, intravascular coagulation, and activation of Hageman factor in the blood. Particularly in clinical practice, for example, the blood of a patient after surgical operation is sometimes contaminated with such endotoxin to cause severe sepsis. It is known that leukocytes stimulated with the contaminant endotoxin in the blood of the patient, particularly of the severe patient, release a variety of cytokines such as tumor necrosis factor, interleukin-1, interleukin-6 and interferon, and acid peroxides. It is also known that these excessive cytokines give physiologically harmful effects.

Columns for removing a variety of components in the blood have been developed so far. As example thereof, there are a column intending to remove leukocytes and granulocytes (Patent Documents 1 and 2), a column intending to absorb the cytokine (Patent Documents 3 and 4), and a column intending to absorb leukocytes and toxin simultaneously (Patent Documents 5 and 6). However, none of them can simultaneously remove the humoral factor to which the blood cells respond. There has also been reported a filter for removing the leukocytes, whose main body is a certain filter element having a zeta potential of 0 mV or more (Patent Document 7). However the report merely discloses the removal of blood cells. Therefore, with any of these conventional columns, remaining cells have been insufficiently normalized.

Meanwhile, it has been reported that, among the blood components, a variety of substances, particularly latent transforming growth factor-beta (TGF-β), immunosuppressive acidic protein, interleukin-10, tumor necrosis factor (TNF) and prostaglandin E2, and cells such as B cells and macrophages abnormally increase or grow in patients with advanced cancer, and suppress immune functions by, e.g., inhibiting induction and functional expression of cancer specific killer cells (Non-patent Document 1, "Shuyo Men-ekigaku (Tumor Immunology)" pages 89 to 112, 1998 written by Hiromi Fujiwara, published by Chugai Igakusha). Thus, particularly aiming at the patients with cancer, there have been developed procedures to enhance an immune system in the patient by removing these immunosuppressive substances, leading to involution of the tumor and inhibition of tumor growth.

As a technology for removing these immunosuppressive substances efficiently and safely, there are disclosed the technologies intending to absorb TGF-β (Patent Documents 8 and 9), carcinoembryonic antigen (Patent Document 10), and immunosuppressive acidic protein (Patent Document 11). However, the technology to efficiently remove these immunosuppressive substances using one absorbent has not been developed yet.

The column described above typically has a filtering element or an absorbent (absorbent carrier) for removing or absorbing each target substance inside the column, and a variety of substances and shapes are used. For example, in Patent Document 1, a nonwoven fabric obtained by mixing fibers having a plurality of fiber diameters for preventing clogging with blood cells is used. However, the nonwoven fabric itself has a high bulk density, and insufficiently controls the removal of blood cells. Thus, the increase of pressure loss upon blood circulation is still concerned.

In the absorbent carrier composed of cellulose acetate beads having diameters of about 2 mm (Patent Document 2), pressure loss is not much concerned. However, it is impossible to enlarge an absorption surface area of the carrier, and this carrier is thus inefficient as the absorbent carrier. Reduction of particle diameter, however, leads to the increase of pressure loss, and thus such a reduction of diameter is not adoptable.

In Patent Document 6, it is disclosed that the bulk density of the absorbent carrier is adjusted to 0.05 to 0.15 $g/cm^3$ for clogging prevention and keeping its configuration. However, this absorbent carrier is poor in practicability, and particularly morphological stability is insufficient.

Nonpatent Document 1: "Shuyo Men-ekigaku (Tumor Immunology)" pages 89 to 112, 1998 written by Hiromi Fujiwara, published by Chugai Igakusha.
Patent Document 1: JP Sho-60-193468-A
Patent Document 2: JP Hei-5-168706-A
Patent Document 3: JP Hei-10-225515-A
Patent Document 4: JP 2000-237585-A
Patent Document 5: JP 2002-113097-A
Patent Document 6: JP 2002-172163-A
Patent Document 7: JP Hei-6-142196-A
Patent Document 8: JP 2003-339854-A
Patent Document 9: JP 2004-248950-A
Patent Document 10: JP 2003-310751-A
Patent Document 11: JP 2003-111834-A

DISCLOSURE OF INVENTION

Problem to be Solved by the Invention

A first object of the present invention is to remove cells such as granulocytes and monocytes and not leave cytokines which promote activation of residual cells in remaining liquid component. The inventors contemplated to accomplish this object by imparting to an absorbent a function of simultaneously removing the cells and the cytokine which has been abnormally increased. That is, it is a first object of the present invention to provide a material capable of being used suitably for simultaneous absorption and simultaneous removal of the cells and the cytokine, and a blood processing column using the material.

The present inventors have obtained a finding that it is important to improve a state of endotoxin-containing blood by absorbing and removing endotoxin present in body fluid, which causes cytokine release, and endotoxin adhered to the surface of granulocytes and monocytes, or preventing the production of excessive cytokine by endotoxin. Based on this finding, the first object of the present invention includes: (1) directly absorbing endotoxin in the body fluid into the absorbent, for direct removal of endotoxin; and (2) absorbing the granulocytes or the monocytes from the blood, for indirectly removing the endotoxin adhered to leukocyte components such as granulocytes or monocytes. The first object also includes (3) removing the cytokine attributed to the endotoxin, for preventing the increase of cytokine concentration in the blood.

In summary, the aforementioned first object of the present invention includes providing a high performance material capable of being used suitably for the absorption and the removal of both the cells such as granulocytes or monocytes and the cytokines, and the endotoxin, and providing a high performance blood processing column using the material.

A second object of the present invention is to remove an immunosuppressive substance involved in cancer cell growth. That is, in the light of the aforementioned problems of the prior art, it is the second object of the present invention to provide a material which is available for general use, which is capable of selectively absorbing directly from the body fluid the immunosuppressive substance such as TGF-β and immunosuppressive acidic protein with high efficiency and removing the leukocytes in the body fluid to bring a leukocyte balance close to a normal balance, and which is capable of being used for extracorporeal circulation safely. This second object includes providing a column for cancer therapy in which the material absorbing such an immunosuppressive substance has been filled, and performing the cancer therapy using the column.

A third object of the present invention is to assure stable availability as the column for blood circulation. That is, in the light of the aforementioned problems of the prior art, it is the third object of the present invention to provide an absorbent carrier which can remove activated leukocytes such as granulocytes and monocytes, and cancer cells and further remove the cytokine which are excessively present, with less pressure loss, as well as to give configuration stability to the carrier itself without impairing the absorption property.

Means for Solving Problem

In order to accomplish the aforementioned first object of the present invention, the present invention includes the following constitutions.

(1) An absorbent having a zeta potential of −20 mV or more and having an ability to absorb granulocytes, monocytes and cytokine in blood.

(2) The absorbent according to (1) above wherein an absorption rate for the granulocytes from the blood is 50% or more and an absorption rate for the monocytes from the blood is 50% or more.

(3) The absorbent according to (1) or (2) above wherein an absorption rate for lymphocytes is 40% or less.

(4) The absorbent according to any of (1) to (3) above wherein the cytokine is at least one selected from the group consisting of interleukin-1 (IL-1), interleukin-6 (IL-6), interleukin-8 (IL-8), interleukin-10 (IL-10), TNF-α, transforming growth factor-beta (TGF-β), vascular endothelial growth factor (VEGF) and immunosuppressive acidic protein (IAP).

(5) The absorbent according to any of (1) to (4) above wherein the absorption rate for coagulation factor XIII is 30% or less.

(6) The absorbent according to (1) above characterized in having the zeta potential of −15 mV or more, and having an absorption capacity for absorbing 90% or more lipopolysaccharide (LPS) in saline in which 1% by volume of fetal calf serum (FCS) has been dissolved.

(7) The absorbent according to any of (1) to (6) above having a quaternary ammonium salt and/or a straight amino group bound to a water-insoluble carrier.

(8) The absorbent according to any of (1) to (7) above wherein the water-insoluble carrier has a shape selected from a fiber, a membrane, a hollow fiber and a bead.

(9) The absorbent according to any of (1) to (8) above wherein the water-insoluble carrier has a shape of is fiber or hollow fiber, the diameter thereof exceeding 3 μm.

(10) The absorbent according to claim 9 above comprising a fiber A having the fiber diameter of 4 to 8 μm and a fiber B having the fiber diameter of 10 to 50 μm.

(11) The absorbent according to claim 10 above wherein the fiber A comprises fibers having the fiber diameter of 4.5 to 8 μm.

(12) The absorbent according to any of (1) to (8) above wherein the water-insoluble carrier has a shape of a bead, and a surface of the material has a protrusion having a diameter of longer than 3 μm.

(13) The absorbent according to any of (1) to (12) above characterized by being used for leukapheresis therapy.

(14) A blood processing column comprising a container and the absorbent according to any of (1) to (13) above filled therein.

(15) The blood processing column according to (14) wherein the blood is circulated therethrough.

(16) The blood processing column according to (14) or (15) characterized by being used for leukapheresis therapy.

(17) The blood processing column according to any of (14) to (16) above wherein an extracorporeal circulation therethrough with a living body results in increase in a number of lymphocytes and decrease in a number of granulocytes, said numbers being measured 150 to 180 hours after finishing the extracorporeal circulation and compared with those before the extracorporeal circulation.

In order to accomplish the aforementioned second object of the present invention, the present invention includes the following constitutions.

(1) An absorbent for cancer therapy comprising a water-insoluble polymer having a hydrophilic amine residue bound thereto, said absorbent having a capacity to absorb latent transforming growth factor-β and a capacity to absorb leukocyte.

(2) The absorbent for cancer therapy according to (1) above wherein the shape of said water-insoluble polymer having the hydrophilic amine residue bound thereto is a membrane, a fiber or a granular matter.

(3) An extracorporeal circulation column for cancer therapy, utilizing the absorbent for cancer therapy according to (1) or (2) above.

In order to accomplish the aforementioned third object of the present invention, the present invention includes the following constitutions.

(1) An absorbent carrier characterized in having at least a bilayer structure of a net and a nonwoven fabric.

(2) The absorbent carrier according to (1) above, wherein the net is a net having 10 mm$^2$ or more voids per 100 mm$^2$.

(3) The absorbent carrier according to (1) above having an ability to absorb a physiologically active substance and/or cells.

(4) The absorbent carrier according to any of (1) to (3) above, wherein the net is composed of a monofilament.

(5) The absorbent carrier according to any of (1) to (4) wherein a bulk density is 0.02 g/cm$^3$ or more.

(6) A blood processing column comprising a cylindrical container and the absorbent according to any of (1) to (5) above filled therein.

(7) The blood processing column according to (6) above for use in blood circulation.

Effect of the Invention

According to the present invention, there are provided an absorbent and a column for blood processing which are useful for blood processing and therapeutic treatment of ulcerative colitis, Crohn's disease and autoimmune diseases by simultaneously removing excessively proliferating leukocytes such as granulocytes and monocytes unnecessary for the living body and the cytokine which transmits information to these cells.

According to the present invention, there are also provided an absorbent and a column for blood processing which are useful for blood processing and therapeutic treatment of ulcerative colitis, Crohn's disease and autoimmune diseases by simultaneously removing excessively proliferating leukocytes such as granulocytes and monocytes unnecessary for the living body and the cytokine which transmits the information to these leukocytes, and simultaneously removing LPS which activates the leukocytes.

According to the present invention, there are also provided an absorbent for cancer therapy which is capable of selectively absorbing an immunosuppressive substance such as TGF-β and immunosuppressive acidic protein directly from the body fluid with high efficiency, and also capable of simultaneously remove the leukocytes in the body fluid, as well as an extracorporeal circulation column for the cancer therapy utilizing the absorbent. Therefore, according to the present invention, it is possible to treat the advanced cancer, prolong the life of the patient and enhance QOL.

According to the present invention, there is further provided an absorbent carrier (absorbent) which causes less pressure loss upon blood circulation, has excellent configuration stability and can be used suitably for a variety of columns for processing the blood. The absorbent carrier is particularly suitable for simultaneously removing the leukocytes and the cancer cells excessively present in and unnecessary for the human body and physiologically active substances such as cytokines, and is useful for the blood processing and the therapeutic treatment of autoimmune diseases, cancers and allergy. This material can be suitably used in a form of a molded article such as a petri dish, a bottle, the membrane, the fiber, the hollow fiber, a granular matter or an assembly by the use thereof as a column for affinity chromatography, a blood column for treatment and particularly an extracorporeal circulation column.

BEST MODE FOR CARRYING OUT THE INVENTION

Subsequently, the present invention will be described in more detail.

As a basic constitution of the absorbent, preferable are those obtained by immobilizing a functional group on a water-insoluble carrier, or those obtained by coating a substrate with a water-insoluble carrier having a functional group immobilized thereon.

The water-insoluble carrier used in the present invention is not particularly limited as long as it is insoluble in water and a functional group can be immobilized thereon. Preferable are olefin-based resins such as polypropylene and polyethylene in terms of biocompatibility. Particularly, polyester typified by polyamide and polyethylene terephthalate is preferable.

It is preferable that the absorbent of the present invention has a high zeta potential in order to recognize sialic acid and phosphoric acid on a glycoprotein on a cell surface, or to recognize sialic acid and phosphoric acid on a sugar chain bound to the cytokine. Usual polymer materials such as polypropylene, polyethylene and polyethylene terephthalate have a negative zeta potential, e.g., about −30 mV. Thus the present inventors set the zeta potential of the water-insoluble carrier to −20 mV or more by immobilizing thereon a particular functional group e.g., a quaternary ammonium salt and/or a straight amino group, and have found that such a carrier exhibits a good absorption property, to thereby reach the present invention. The zeta potential is preferably −15 mV or more, because thereby the absorption property for lipopolysaccharide (LPS) becomes more excellent. The zeta potential of −10 mV or more results in the higher effect, and the zeta potential of −2 mV or more is further preferable.

In the present invention, it is preferable to have an absorption capacity to absorb the granulocyte, the monocyte and the cytokine and simultaneously have the absorption capacity to absorb LPS. LPS is, as described below, a toxin which gram-negative bacteria generally have. It has been found out that LPS is bound to a receptor protein such as TLR-4 on the leukocyte and activates the protein. When the granulocyte, the monocyte and the cytokine are removed, abnormal states caused by them can be reduced. However, when LPS which have generated by the bacteria present in an inflammatory site or an ulcer site remains, even if a patient has almost recovered, the patient may fall into the abnormal state again. The absorbent of the present invention becomes useful for efficient blood processing and therapeutic treatment of ulcerative colitis, Crohn's disease and autoimmune diseases by imparting thereto the mechanism preferable for removing LPS simultaneously with the absorption of the leukocyte and the cytokine. By using such a multifunctional absorbent, it is possible to reduce the size of the column for treatment.

In the present invention, the "zeta potential" refers to the zeta potential on the surface of the absorbent. The surface zeta potential can be calculated by measuring a fluid potential, pressure applied to run a fluid and a specific conductivity of the fluid. The zeta potential on the absorbent of the present invention is preferably −20 mV or more, more preferably −15 mV or more and particularly preferably −2 mV or more. The upper limit is preferably 10 mV or less in terms of preventing hemolysis of erythrocytes.

Although the shape of the water-insoluble carrier is not particularly limited in the present invention, the carrier is preferably in a form of a fiber, a membrane, a hollow fiber or a bead, in terms of workability and pressure loss in the blood processing column. The shape may also be, of course, combinations thereof.

The absorbent in the present invention has the capacity to absorb the granulocytes, the monocytes and the cytokine in blood. Particularly, it is preferable that the absorption rate for the granulocytes from blood is 50% or more and the absorption rate for the monocytes is 50% or more. The absorption rate in the present invention may be measured by, when that for the blood cells is taken as an example, passing blood once through the column filled with the absorbent, and counting the number of the blood cells before and after the passage using a hemocytometer. The rate is calculated in accordance with the formula mentioned below. Conditions, e.g., the size and shape of the column, and the passing speed of blood can be appropriately determined in accordance with the Examples.

Absorption rate (%)=[(number of blood cells in blood before passing through column)−(number of blood cells in blood after passing through column)]/(number of blood cells in blood before passing through column)×100

The absorbent of the present invention having a function of absorbing the blood cells may also have a function of filtration. In this case, the aforementioned absorption rate is calculated based on not only the amount of blood cells removed from blood by absorption but also the amount of the blood cells removed by filtration.

In order to absorb and remove the cells such as granulocytes and monocytes, it is preferable that the absorbent of the present invention is in a form of a water-insoluble carrier. Particularly, it is preferable that the carrier has a fiber diameter of the fiber or the hollow fiber, or a diameter (size) of the protrusion on the surface of a bead particle exceeding 3 μm. When the diameter is smaller than this, the absorption and removal of lymphocytes may increase, leading to the removal of memory cells, which is not preferable. However, in order to reduce the absorption and removal rate of the lymphocytes, the diameter of the fiber is more preferably 4 μm or more and still more preferably 4.5 μm or more. Further, in order to reduce the lymphocyte removal rate while keeping the removal rates for the granulocytes and the monocytes, sometimes the diameter of the fiber may preferably be 5 μm or more. However, when the diameter of the fiber exceeds 8 μm, the removal rate of the granulocytes and the monocytes tends to decrease, and when the diameter of the fiber is 10 μm or more, the removal rate of the granulocytes and the monocytes decreases. Thus, such a large diameter is not preferable. It is preferable in terms of practical use that the diameter of the fiber is 20 μm or less.

With the aforementioned fiber (referred to as the fiber A), a fiber having the larger diameter (referred to as the fiber B) may be mixed for the purpose other than the removal of the blood cells, i.e., as a fiber structural body for keeping strength of the absorbent at not less than a certain level. The diameter of such a fiber B is not limited to the aforementioned, and is preferably 10 to 50 μm. When the diameter is smaller than 10 μm, the fiber B may be unable to exert the expected purpose thereof, i.e., the effect of keeping the strength. When the diameter exceeds 50 μm, it becomes difficult to mix with the fiber A.

The removal rate for the lymphocytes (absorption rate using the absorbent of the present invention) is preferably 40% or less because of less tendency of memory cell reduction, and it is preferably 30% or less in terms of safety.

The absorbent of the present invention may preferably be those obtained by immobilizing a quaternary ammonium salt and/or a straight amino group as a functional group on the aforementioned water-insoluble carrier. Examples of reactive functional groups for immobilizing the quaternary ammonium salt and/or the straight amino group to the water-insoluble carrier may include active halogen groups such as a halomethyl group, a haloacetyl group, a haloacetamidemethyl group and a halogenated alkyl group, an epoxide group, a carboxyl group, an isocyanic acid group, a thioisocyanic acid group, and an acid anhydrate group. Especially the active halogen groups, and further among them, haloacetyl group is preferable because its production is easy, the reactivity is appropriately high, an immobilization reaction of the quaternary ammonium salt and/or the straight amino group can be performed under a mild condition, and a covalent bond generated by this reaction is chemically stable.

As the immobilized functional group, the quaternary ammonium salt and/or the straight amino group is suitable, and these mean the state in which ammonia and/or primary to tertiary amino group has been chemically bound to a polymer. Furthermore, as the primary to tertiary amino groups, those having 18 or less carbon atoms per one nitrogen atom are preferable for enhancing a reaction rate. Furthermore, those having, among the primary to tertiary amino groups, the immobilized quaternary ammonium group that have been formed by binding the tertiary amino group having an alkyl group having 3 to 18 carbon atoms, particularly 4 to 14 carbon atoms per one nitrogen atom are excellent in absorbability of the cytokines. Specific examples of such a tertiary amino group may include trimethylamine, triethylamine, N,N-dimethylhexylamine, N,N-dimethyloctylamine, N,N-dimethyllaurylamine and N-methyl-N-ethyl-hexylamine. Examples of compounds having the straight amino group may include tetraethylenepentamine.

The density of the bound quaternary ammonium salt and/or straight amino group in the present invention may vary depending on a chemical structure and an intended use of the water-insoluble carrier. When the density is too low, its function does not tend to occur. When the density is too high, the physical strength of the carrier after the immobilization worsens and the function as the absorbent tends to be deteriorated. Thus, the density is preferably 0.01 to 2.0 mol and more preferably 0.1 to 1.0 mol per repeating unit of the water-insoluble carrier. As the method for immobilizing the quaternary ammonium salt and/or the straight amino group (quaternizing), a reaction using potassium iodide as a catalyst is often used. However, the method is not limited thereto, and the publicly known method may also be used.

The cytokine absorbed by the absorbent of the present invention is at least one cytokine selected from the group consisting of interleukin-1 (IL-1), interleukin-6 (IL-6), interleukin-8 (IL-8), interleukin-10 (IL-10), tumor necrosis factor-α (TNF-α), transforming growth factor-beta (TGF-β), vascular endothelial growth factor (VEGF) and immunosuppressive acidic protein (IAP). All of these cytokines are pointed out to be involved in pathology of immune diseases such as ulcerative colitis, Crohn's disease and chronic rheumatoid arthritis which are considered to be indications for the leukapheresis therapy.

The quaternary ammonium salt and/or the straight amino group to be immobilized may be appropriately selected depending on the type of the cytokine to be absorbed. For example, absorbability for interleukin-1 (IL-1), interleukin-6 (IL-6), transforming growth factor-beta (TGF-β), vascular endothelial growth factor (VEGF) and immunosuppressive acidic protein (IAP) may be imparted by immobilizing N,N-dimethylhexylamine, N,N-dimethyloctylamine or N,N-dimethyllaurylamine. Absorbability for interleukin-8 (IL-8), interleukin-10 (IL-10) and tumor necrosis factor-α (TNF-α) may be imparted by immobilizing tetraethylenepentamine as an amine component. It is possible to immobilize a plurality of sorts of functional groups in combination. For example, it is possible to use both the quaternary ammonium salt and the straight amino group. By using such a combination of a plurality of sorts of functional groups, the range of cytokine types to be absorbed can be expanded, which is preferable. Additionally there is an advantage in that the absorption property for the desired cytokine is enhanced.

In the present invention, the ability for the absorption and removal of these cytokines may be evaluated based on the results of measurement by EIA method (enzyme immunoassay) using natural types of proteins in all cases (conditions: shaking at 37° C. for 2 hours to achieve batch absorption). For example, for IL-6, it is preferable that the absorption rate measured by the batch absorption shown in Example is 50% or more. Furthermore, in order to reduce the effect on residual cells, it is preferable that the absorption rate is 60% or more. For example, for IL-1, it is preferable that the absorption rate measured by the batch absorption shown in Example is 40% or more. Furthermore, in order to reduce the effect on residual cells, it is preferable that the absorption rate is 50% or more.

As described above, there is no particular limitation on the shape of the absorbent. Upon use in a column, preferable shape of the absorbent may be beads, fibers, hollow fibers, and fibrous structures such as knitted fabrics obtained by knitting the fiber, woven fabrics and nonwoven fabrics. If the water-insoluble carrier can keep its configuration by itself, it is possible to use it alone. If the water-insoluble carrier has poor configuration stability, the carrier can be fixed to an appropriate substrate by coating the carrier. Alternatively, the carrier may be combined with another absorbent and put in a column for use. Operations such as fixation and combining may be performed before configuring the aforementioned shape.

In the absorbent of the present invention, it is particularly preferable that its shape is the nonwoven fabric. In that case, when the bulk density of the nonwoven fabric is too large, the clogging easily occurs, and conversely when the bulk density is too small, the absorbent becomes poor in its configuration stability. Thus, the bulk density is preferably $0.02$ g/cm$^3$ or more, particularly it is preferable to be $0.02$ g/cm$^3$ or more, and it is more preferably to be $0.05$ g/cm$^3$ or more. The upper limit is preferably $0.15$ g/cm$^3$ or less.

Although the nonwoven fabric used in the present invention may be made of a single fiber, it is particularly preferable that the nonwoven fabric is made from a sea-island type composite fiber. That is, the absorbent can be easily produced by preparing a nonwoven fabric composed of such a composite fiber in accordance with any publicly known method, giving needle punching to this nonwoven fabric, and then dissolving the sea component in order to control the bulk density and to enhance the configuration stability.

In addition, the nonwoven fabric may be in a form of a bilayer structure with a net which will be described later. Particularly, the structure may be composed of a net and the nonwoven fabric enfolding the net. By employing such a structure, it is possible to enhance the configuration stability when the fabric is rolled up to be a cylindrical shape for use in a column.

Preferable materials as the water-insoluble carrier are hydrophobic fibers, e.g., polyolefin such as polyethylene and polypropylene, polyester such as polyethylene terephthalate and polybutylene terephthalate, and fluorinated polymer such as Teflon. In addition, those to which a variety of alkyl groups have been added by surface modification for providing a hydrophobic site may also be used. Specific examples of the suitable polymer which can be used alone for immobilizing the quaternary ammonium salt and/or the straight amino group may include polysulfone based polymers such as poly (p-phenylene ether sulfone)-$\{(p\text{-}C_6H_4)\text{—}SO_2\text{-}(p\text{-}C_6H_4)\text{—}O\text{-}\}n\text{-}$, UDEL polysulfone-$\{(p\text{-}C_6H_4)\text{—}SO_2\text{-}(p\text{-}C_6H_4)\text{—}O\text{-}(p\text{-}C_6H_4)\text{—}C(CH_3)_2\text{-}(p\text{-}C_6H_4)\text{—}O\}_n\text{—}$, $\text{-}\{(p\text{-}C_6H_4)\text{—}SO_2\text{-}(p\text{-}C_6H_4)\text{—}O\text{-}(p\text{-}C_6H_4)\text{—}O\}_n\text{—}$, $\text{-}\{(p\text{-}C_6H_4)\text{—}SO_2\text{-}(p\text{-}C_6H_4)\text{—}SO_2\text{-}(p\text{-}C_6H_4)\text{—}O\}_n\text{—}$, $\text{-}\{(p\text{-}C_6H_4)\text{—}SO_2\text{-}(p\text{-}C_6H_4)\text{—}O\text{-}(p\text{-}C_6H_4)\text{—}C(CF_3)_2\text{-}(p\text{-}C_6H_4)\text{—}O\}_n\text{—}$, polyether imide, polyimide, polyamide, polyether, polyphenylene sulfide, polystyrene and acryl polymers, with a proviso that the polymers have a reactive functional group for immobilizing the amino group by covalent bond. Among them, the polysulfone based polymers are preferably used because of its high stability and good configuration stability.

Specific examples thereof may include chloroacetamide methylated polystyrene, chloroacetamide methylated-UDEL polysulfone and chloroacetamide methylated polyether imide to which the aforementioned reactive functional group has been bound. Among these polymers, those which are soluble in an organic solvent are particularly preferable in terms of moldability.

The absorbent of the present invention may be produced by molding the polymer itself having such a quaternary ammonium salt and/or straight amino group, i.e. the water-insoluble carrier itself, into the shape of fiber, the hollow fiber or the bead. Alternatively, the absorbent of the present invention may also be produced by coating the substrate composed of the fiber, the hollow fiber or the bead, preferably the nonwoven fabric in terms of productivity, with the polymer having the quaternary ammonium salt and/or straight amino group. Upon such coating, the polymer may be dissolved in a solvent, e.g., methylene chloride, tetrahydrofuran or N,N-dimethylformamide to prepare a solution. The product may be easily produced by immersing the nonwoven fabric in the solution, and then evaporating the solvent.

As a reaction solvent when the quaternary ammonium salt and/or straight amino group is immobilized to the water-insoluble carrier, water, methanol, ethanol, isopropanol, dimethylsulfoxide, N,N-dimethylformamide, N,N-dimethylacetamide and N-methylpyrrolidone are preferably used.

It is preferable that the absorbent and the blood processing column of the present invention do not reduce the activity of the blood coagulation factor XIII (coagulation XIII factor) upon blood processing in consideration of their safety. Particularly, the level of the blood coagulation factor XIII tends to lower in the patients with ulcerative colitis and Crohn's disease, and shortage of this factor may result in bleeding tendency. If the absorption rate for the blood coagulation factor XIII is 30% or less, they can be used safely. More preferably, the absorption rate is 20% or less. Such an absorption rate can be measured by calculating a ratio of a carrier amount with respect to the amount of actually processed blood (in the present invention, the blood includes whole blood, plasma, serum, ascites and pleural effusion), preparing a plasma from blood collected with citric acid from a healthy volunteer, and measuring the activities of the blood coagulation factor XIII therein before and after shaking at 37° C. for one hour. The activity of blood coagulation factor XIII can be measured by a synthetic substrate method, although the measurement may be entrusted to a professional company.

The absorbent and the blood processing column of the present invention may have an absorption capacity to absorb 90% or more lipopolysaccharide (LPS) in saline containing 1% by volume fetal calf serum (FCS). Having the absorption capacity for lipopolysaccharide in this manner, it is possible to prevent the production of excessive cytokines due to the endotoxin contaminated in blood of the patient after the surgical operation or contaminated from the inflammatory site or the ulcerous site. In addition, it is also possible to efficiently absorb the endotoxin itself to thereby obtain preventive or therapeutic effects on fever, shock, intravascular coagulation and lymphocyte activation derived from the biological activity of the endotoxin. Therefore, the preventive or therapeutic effects on fever, shock, intravascular coagulation and lymphocyte activation derived from the biological activity of the endotoxin can be obtained, and the absorbent thus becomes useful particularly for the immunostimulatory therapy. Furthermore, by having the absorption capacity for lipopolysaccharide and the absorption capacity for the granulocytes, the monocytes and the cytokines in combination, it is possible to perform simultaneous process with one absorbent, which is also preferable.

"Lipopolysaccharide" means a molecule containing the structure of lipid A. Examples of typical LPS that may present in blood may include a toxin from gram-negative bacteria.

It is known that when the endotoxin is present in an excessive amount in blood, it causes an excessive release of a variety of cytokines such as tumor necrosis factor, interleukin-1, interleukin-6 and interferon, and acid oxide from leukocytes. By further imparting the absorption capacity for lipopolysaccharide to the absorbent of the present invention, it is also possible to enhance the production of interferon-$\gamma$ which is thought to be attributed to the activation of lymphocyte, particularly Th1 lymphocytes. The absorbent and the blood processing column of the present invention thereby becomes useful in the immunostimulatory therapy. Although the mechanism for the activation of such lymphocytes is unknown in detail, it is thought that the activation is attributed to the contact of the blood cells in the processed blood with absorbed LPS.

The amount of absorbed LPS can be measured using a toxinometer supplied from Wako Pure Chemical Industries Ltd. The removal amount and the removal rate can be obtained by mixing LPS in a defined amount in saline containing 1% by volume FCS, and measuring the amount of LPS left in a supernatant after incubating in a water bath at 37° C. for 4 hours. By calculating a difference and a ratio between the measured amount and the amount of the LPS in the LPS-added solution which has similarly been measured using the toxinometer, the removal amount and the removal rate may be obtained. The removal amount is desirably 100 pg/mg and more preferably 200 pg/mg. The ability of the present invention to simultaneously absorb the granulocytes and/or the monocytes and the cytokine in the body fluid and absorb LPS in saline containing 1% by volume FCS can also be realized by combining the distinct absorbents. In this case, the respective absorbents may be taken together to fill one column, or each absorbent may be filled in the separate column to constitute a cassette of columns. Since the cassette of columns tend to be in a non-compact constitution, an embodiment in a unified constitution is more convenient. The present invention is not limited to the aforementioned examples, and it is possible to appropriately select suitable constitution.

The column for blood processing of the present invention may be produced by filling a column container with the absorbent of the present invention. As the column container, it is possible to use publicly known containers for the column for blood processing. Preferable constitution of the column may be: a column in which the absorbent formed in a form of flat plates are stacked and filled; a column in which a cylindrical filter composed of the absorbent rolled up into a cylindrical shape is housed in a cylindrical container having a blood inlet and a blood outlet at both ends; and a column in which a hollow cylindrical filter composed of the absorbent rolled up into a cylindrical shape with both ends sealed is housed in a cylindrical container having a blood inlet and a blood outlet, the blood outlet of the container being provided at the site leading to an outer circumference of the hollow cylindrical filter and blood outlet of the container being provided at the site leading to an inner circumference of the hollow cylindrical filter. Among them, the column having the hollow cylindrical filter is the most preferable because of efficient removal of the inflammatory leukocytes since most of inflammatory leukocytes in blood are rapidly removed by the nonwoven fabric having a large area on the outer circumference of the cylindrical filter, and remaining few leukocytes coming to the inner circumference of the cylindrical filter and are thoroughly removed by the nonwoven fabric having a small area. When the absorbent of the present invention is in a form of a nonwoven fabric, it is possible to enhance the configuration stability by, upon preparing the extracorporeal circulation column for the cancer therapy, making the below-mentioned bilayer structure with a net, preferably making a structure in which the net is enfolded with the nonwoven fabric and then rolled up into the cylindrical shape.

The column for blood processing of the present invention can be used for the leukapheresis therapy and the immunostimulatory therapy. As described later, as a result of the extracorporeal circulation with the living body using the column for blood processing of the present invention, after 150 to 180 hours have passed since the termination of the extracorporeal circulation, the number of the leukocytes, particularly the number of granulocytes in blood becomes smaller and the number of the lymphocytes becomes larger than the numbers before the extracorporeal circulation. This suggests that the column for blood processing of the present invention has a function of reforming the immune state. Particularly, it is known that, in a patient with advanced cancer, the number of the granulocytes increases and the number of the lymphocytes decreases, whereby the immune state is suppressed. By the use of the present column, the state is reformed to the normal state. This effect does not remain for a long period of time after the extracorporeal circulation. After the lapse of approximately one week, the number of the granulocytes tends to increase whereas the number of the lymphocytes tends to decrease. Thus, it is desirable to give this procedure about once a week.

Meanwhile, the absorbent of the present invention can be used for the cancer therapy, and the present invention also provides the absorbent for the cancer therapy. Subsequently, the absorbent for the cancer therapy of the present invention will be described in more detail.

In the present invention, an immune function suppressive protein refers to a protein present in blood, which suppresses an immune function in mammalian animals, e.g., TGF-$\beta$, the immunosuppressive acidic protein, interleukin-10 and TNF-$\alpha$.

When the absorbent of the present invention is used as the absorbent for the cancer therapy, the absorbent may be those having an ability to absorb an immunosuppressive protein (immune function suppressive protein). The larger the absorption capacity is, the smaller amount of blood for extracorporeal processing is required, which is thus preferable. For obtaining rough evaluation of the absorption capacity of the absorbent for the cancer therapy and the extracorporeal circulation column for the cancer therapy which will be described later, latent transforming growth factor-$\beta$ (latent TGF-$\beta$) which is TGF-$\beta$ in blood may be used a standard substance. As to the absorption capacity of the extracorporeal circulation column for the cancer therapy, it is desirable that the column is capable of absorbing 100 ng or more of latent TGF-$\beta$ per kg bodyweight in the tumor-bearing mammalian animal. For application to a patient with advanced cancer, it is desirable to absorb 250 ng or more because the concentration of the substances to be absorbed in blood is increased in such a patient. The absorption capacity may be calculated by multiplying an equilibrium absorption amount of latent TGF-$\beta$ per one gram of the absorbent, by a filled amount (gram) of the absorbent in the column.

The equilibrium absorption amount of latent TGF-$\beta$ in the present invention is a value obtained by adding 30 mg of the absorbent for the cancer therapy to 1 mL of serum from a tumor-bearing rat, shaking it at 37° C. for 4 hours, then measuring the concentration of TGF-β in the supernatant, and dividing a concentration difference between before and after the absorption by the weight (0.03 g) of the absorbent for the cancer therapy. The concentration of TGF-β in the supernatant can be obtained by pretreating the sample serum with acid to convert latent TGF-β into free TGF-β, and then measuring the TGF-β level by an enzyme immunoassay using anti-TGF-β antibody. In the case of latent TGF-β, the absorption rate is preferably 40% or more under the condition of the batch absorption method described in the Examples. The absorption rate is more preferably 50% or more in order to reduce the influence to the immunosuppressive effect. Commercially available kits may be used for measuring the concentration of TGF-β. It is known that there are superfamily members of TGF-β which are different in sequences thereof, such as TGF-β1, TGF-β2, TGF-β1.2, TGF-β4 and TGF-β5. The amino acid sequences thereof are highly homologous, and their natures when absorbed to the absorbent are similar. The nature of TGF-β is basically represented by the nature of TGF-β1. Thus, for its quantification, the kit for measuring TGF-β1 is particularly commonly used.

In the present invention, the tumor-bearing mammalian animal means land mammalian animals such as human beings, monkeys, cattle, horses, dogs, cats, swines and sheeps that bear a tumor.

Such an absorbent for the cancer therapy of the present invention can be used as an extracorporeal circulation column for the cancer therapy. The smaller the amount of the absorbent for absorbing the immunosuppressive protein for the cancer therapy which is filled in the extracorporeal circulation column for the cancer therapy of the present invention is, the smaller amount of blood to be processed extracorporeally is needed, which is thus preferable. However, when the amount is too small, the absorption capacity is decreased and the effect is lost. When it is too large, a burden on the living body is increased. In general in terms of safety, it has been reported that the adequate amount of blood to be circulated in an extracorporeal circuit upon extracorporeal circulation is permitted up to 200 mL which is the amount permitted when blood is collected for blood infusion. The amount of the whole blood in a person with a body weight of 60 kg is about 4.6 L. Thus, it is acceptable that the amount of blood to be processed extracorporeally is 4% or less of the whole blood amount. Meanwhile, when the absorbent is filled in the column, a void ratio of 15% or more is required for passing blood. From these conditions, the material for absorbing the immunosuppressive protein may be preferably filled in the column at an amount of 0.05 g or more and 3.5 g or less per kg of bodyweight of the tumor-bearing mammalian animal.

The absorbent for the cancer therapy and the extracorporeal circulation column for the cancer therapy according to the present invention can simultaneously absorb and remove the leukocytes such as granulocytes and monocytes which have increased in blood. It is desirable to have a high removal performance for the granulocytes and the monocytes. In removal evaluation in vitro, the removal rate is preferably 35% or more and more preferably 50% or more. Particularly, it is preferable that the absorption rates are 50% or more for both granulocytes and monocytes. In order to absorb and remove these granulocytes and monocytes, it is preferable to appropriately select the form of the absorbent for the cancer therapy. Specifically, it is preferable that the form of the absorbent for the cancer therapy is a fiber (including composite yarn and spun yarn, and may be a short fiber or continuous fiber), a membrane, a hollow fiber or a bead. The fiber may be used as an appropriate fiber structure (woven fabrics, knitted fabrics, nonwoven fabrics, flocculent matters). When the form of the nonwoven fabric is employed, such a nonwoven fabric may be configured in a bilayer structure with a net as will be described later, particularly the structure in which the net is enfolded with the nonwoven fabric. By employing such a structure, it is possible to enhance the configuration stability when the column is formed by rolling up into the cylindrical shape.

Particularly, in order to enhance the capacity to absorb and remove the granulocytes and the monocytes, it is preferable that a fiber diameter of the fiber or the hollow fiber, or a diameter (size) of the protrusion on the surface of the bead particle exceeds 3 μm. When the diameter is smaller than this, the absorption and removal of lymphocytes may increase, leading to the removal of memory cells, which is not preferable. However, in order to reduce the absorption and removal rate of the lymphocytes, the diameter of the fiber is preferably 4 μm or more and more preferably 4.5 μm or more. Further, in order to reduce the lymphocyte removal rate while keeping the removal rate for the granulocytes and the monocytes, sometimes the diameter of the fiber may preferably be 5 μm or more. However, when the diameter of the fiber exceeds 8 μm, the removal rate of the granulocytes and the monocytes tends to decrease, and when the diameter of the fiber is 10 μm or more, the removal rate of the granulocytes and the monocytes decreases. Thus, such a large diameter is not preferable. It is preferable in terms of practical use that the diameter of the fiber is 20 μm or less because the removal rate is further decreased when the diameter is 20 μm or more.

However, the diameter of the fiber structural body mixed for the purpose other than the removal of blood cells is not limited to the aforementioned. For example, in addition to the aforementioned fiber (referred to as the fiber A), the fiber having the larger diameter (referred to as the fiber B) may be mixed for the purpose other than the removal of the blood cells, i.e., as the fiber structural body for keeping strength of the absorbent at not less than a certain level. The diameter of such a fiber B is not limited to the aforementioned, and is preferably 10 to 50 μm. When the diameter is smaller than 10 μm, the fiber B may be unable to exert the expected purpose thereof, i.e., the effect of keeping the strength. When the diameter exceeds 50 μm, it becomes difficult to mix with the fiber A.

The removal rate for the lymphocytes (absorption rate using the absorbent of the present invention) is preferably 40% or less because of less tendency of memory cell reduction, and it is preferably 30% or less in terms of safety. Particularly, in the patients with advanced cancer or terminal cancer, it is more preferably 20% or less because the number of the lymphocytes in blood has been decreased in such patients.

The preparation of the extracorporeal circulation column for the cancer therapy of the present invention may be accomplished by filling the absorbent for the cancer therapy of the present invention in a column container. Upon such use, the absorbent for the cancer therapy of the present invention may be in a form of, as described above, the nonwoven fabric, the woven fabric, the knitted fabric, the flocculate, the hollow fiber or the bead. The shape of the container is not particularly limited, and those conventionally used for the extracorporeal circulation column may be employed. The shape is generally cylindrical. When such a cylindrical container is used, the configuration stability of the absorbent for the cancer therapy of the present invention may be enhanced by making the absorbent in a form of the nonwoven fabric, and making a bilayer structure with a net as described later, preferably a structure in which the net is enfolded with the nonwoven fabric and then rolled up into the cylindrical shape, for filling into the column.

The absorbent for the cancer therapy of the present invention comprises a water-insoluble polymer having a hydrophilic amine residue bound thereto. The preparation of the water-insoluble polymer having the hydrophilic amine residue bound thereto may be accomplished by reacting the water-insoluble carrier with hydrophilic amine in a solvent.

Specific examples of the water-insoluble carrier used may include poly(aromatic vinyl compounds) such as polystyrene, polysulfone based polymers such as poly(p-phenylene ether sulfone) and -{(p-$C_6H_4$)—C($CH_3$)$_2$-(p-$C_6H_4$)—O-(p-$C_6H_4$)—$SO_2$-(p-$C_6H_4$)—O-}n- (UDEL polysulfone), polyether imide, polyimide, polyamide, polyether and polyphenylene sulfide, which have a reactive functional group for immobilizing hydrophilic amine. Examples of the reactive functional group for immobilizing hydrophilic amine may include active halogen groups such as a halomethyl group, a haloacetyl group, a haloacetamidemethyl group and a halogenated alkyl group, an epoxide group, a carboxyl group, an isocyanic acid group, a thioisocyanic acid group, and an acid anhydrate group. More specific examples of the water-insoluble polymer may include chloroacetamide methyl polystyrene, chloroacetamide methylated UDEL polystyrene and chloroacetamide methylated polyether imide. Furthermore, if these polymers are soluble in the organic solvent, there is an advantage in terms of moldability.

The hydrophilic amine residue referred to in this invention means a hydrophilic amine which alone is soluble in water or capable of dissolving water therein, the amine being in a state of chemically bound to the polymer. Hydrophilic amine which forms the hydrophilic amine residue may be those having 18 or less carbon atoms per one nitrogen atom.

Particularly excellent are those having bound thereto, among the hydrophilic amines, a quaternary ammonium group obtained from tertiary amine having an alkyl group having 3 to 18 carbon atoms, particularly 4 to 14 carbon atoms per one nitrogen atom. Specific examples of such tertiary amine may include trimethylamine, triethylamine, N,N-dimethylhexylamine, N,N-dimethyloctylamine, N,N-dimethyllaurylamine and N-methyl-N-ethyl-hexylamine. Furthermore, also preferably used as the hydrophilic amine are those having a alkyl group which comprises a hydrophilic group such as hydroxyl group or ether group, for example, N,N-dimethyl-6-hydroxyhexylamine and N,N-dimethyl-4-methoxybutylamine.

The density of the bound hydrophilic amine residue in the present invention may vary depending on the chemical structure of the water-insoluble polymer. When the density is too low, its function does not tend to occur. When the density is too high, the physical strength of the water-insoluble polymer after the immobilization worsens and the function as the absorbent tends to be deteriorated. Thus, the density is preferably 0.01 to 2.0 mol and more preferably 0.1 to 1.0 mol per mol of the repeating unit of the water-insoluble polymer.

A surface area of the absorbent for the cancer therapy of the present invention is preferably 0.1 $m^2$ or more and more preferably 0.3 $m^2$ or more per one gram of the absorbent. Since the surface area can not be expanded infinitely, there is a practical limit thereto. Preferably, the surface area may be 10 $m^2$ or less. This surface area can be measured by mercury porosimetry.

The absorbent for the cancer therapy of the present invention is obtainable by molding the water-insoluble polymer having the hydrophilic amine residue into a form such as membranes, fibers or particles; or coating the substrate having the form such as membranes, fibers or particles with the water-insoluble polymer having the hydrophilic amine residue; or binding the hydrophilic amine residue to an article such as membranes, fibers or particles which has been made of the water-insoluble polymer.

There are some methods for producing the article of the water-insoluble polymer having the hydrophilic amine residue bound thereto, one of which is a heterogeneous system reaction in which a solution of hydrophilic amine is contacted with the article of the water-insoluble polymer; and another one of which is a homogeneous system reaction in which the solution of the water-insoluble polymer and the solution of hydrophilic amine are mixed and reacted and then molded. As an example of the method for the heterogeneous system reaction, the reaction may be easily accomplished by immersing the article such as fibers or hollow fibers of chloroacetamide methylated polysulfone in a solution containing dimethylhexylamine or polyalkylene imine in isopropanol, and then reacting at temperature of 0 to 100° C. As an example of the method of the homogeneous system reaction, the reaction may be accomplished by adding corresponding polyamine into the solution of chloroacetamide methylated polysulfone and reacting at temperature of 0 to 100° C. Although the amount thereof is not particularly limited, it is preferable to use one fold mol or more relative to the haloacetamide methyl group for obtaining a soluble polymer. Particularly, for obtaining a soluble polymer of polyamine, it is preferable to use hydrophilic amine in an extremely excessive amount.

As the reaction solvent, the highly polar solvents such as water, methanol, ethanol, isopropanol, dimethylsulfoxide and N,N-dimethylformamide (DMF) are advantageous for accelerating the reaction. In the heterogeneous system reaction, the solvent is not particularly limited as long as hydrophilic amine can be dissolved therein. In the homogeneous reaction system, the solvent in which both the water-insoluble carrier and hydrophilic amine are dissolved, specifically, tetrahydrofuran, dimethylsulfoxide, N,N-dimethylformamide, N,N-dimethylacetamide and N-methylpyrrolidone are preferably used. It is also possible to give a surface treatment on the article. For such a treatment, the solvent such as water, methanol or ethanol which does not dissolve polysulfone and dissolves hydrophilic amine is preferably used.

When the surface of the article such as polyester fibers, nylon fibers and polyphenylene sulfide fibers is coated with the water-insoluble polymer of the present invention having the hydrophilic amine residue, it is possible to obtain a high-degree article having a larger surface area is advantageously obtainable with simple and inexpensive manner. Coating can be easily accomplished by immersing the knitted fabric or the woven fabric of nylon in a solution in which the water-insoluble polymer having the hydrophilic amine residue has been dissolved in a solvent having a low boiling point such as methylene chloride or tetrahydrofuran, and then volatilizing the solvent. It is also possible to perform a wet coating method of dissolving the material in a solvent such as N,N-dimethylformamide, which is then placed in a poor solvent of the polymer such as water. The polymer of the molded article to be coated is not particularly limited as long as it has a good adhesiveness with the water-insoluble polymer of the present invention having the hydrophilic amine residue, and may be any of polyamide, polyurethane, polyimide, polysulfone, polyvinyl chloride, and polyester. Although its type is not particularly limited, amide-based polymers such as nylon and polyether imide are preferably used because their adhesiveness is particularly good.

Upon the aforementioned molding or coating on the substrate, it is preferable to employ the form of hollow fiber as the fiber for the molded article or the substrate. Since an absorbent having a function of filtration can be produced thereby, it is advantageous in that the immunosuppressive substance and the leukocytes can be removed when using the product as an artificial dialysis device or a plasma separator.

The extracorporeal circulation column for the cancer therapy of the present invention is used for an extracorporeal circulation therapy of the patients with cancer, particularly advanced cancer for the purpose of inhibiting the progress of the cancer in the tumor-bearing patient or enhancing a quality of life in the patient with cancer. The absorbent of the present invention can also be used for the purpose of removing the immunosuppressive protein when bled blood is refluxed into the body during the surgical operation for cancer removal.

The present invention also provides an absorbent (absorbent carrier) comprising the nonwoven fabric such as those which are described above as a preferable embodiments among the absorbent, and a net combined therewith. That is, the present invention also provides an absorbent (absorbent carrier) having at least a bilayer structure of the net and the nonwoven fabric, which will be described below in detail.

The present inventors has extensively studied on the aforementioned problems, i.e., obtaining an absorbent which can simultaneously and selectively absorb and remove with high efficiency both the cells such as leukocytes or cancer cells and the physiologically active substance such as cytokine which are excessively present in blood, and can be safely used for the extracorporeal circulation. Then the present inventors focused on that the absorbent in the prior art is problematic in its too large bulk density, and that, even if the nonwoven fabric having mere small bulk density is obtained, lack of configuration stability thereof eventually results in occurrence of clogging. The present invention was accomplished on the basis of the foregoing. That is, the present inventors succeeded in both decreasing the bulk density and giving configuration stability.

Examples of the physiologically active substance may include proteins, lipids, sugars and hormones derived from organisms such as chemotaxis, antibodies, complements, lymphokines and other humoral factors, in addition to the cytokines described above. Particularly, the substances selected as the targets of removing works and therapeutic purposes for structural analyses and pattern analyses are subjected. In addition, bacteria, bacterial toxins and viruses which harmfully affect the living body are also addressed as the physiologically active substances. For the cells, mainly blood cells and cancerous cells are subjected, and cells which appear in blood, lymph fluid, and exudates such as ascites and pleural effusion are subjected. Cultured cells, yeast and bacteria in the research are also subjected.

As the material of the nonwoven fabric in the present invention, publicly known polymers such as polyamide, polyester, polyacrylonitrile based polymers, polyethylene and polypropylene can be used. These polymers may be used alone or in composite, e.g., a core shield type, a sea-island type or a side by side type. The shape of the cross section of the fiber may be a circular section or a variant section other than that. As the method for producing the nonwoven fabric, the publicly known method for producing the nonwoven fabric, e.g., a wet method, a carding method, an air lay method, a spun bond method and a melt blow method can be used.

The diameter of the fiber which composes such a nonwoven fabric should be determined in consideration of an aimed absorption performance. For example, for removing the granulocytes, the diameter is preferably more than 3 µm, preferably 4 µm or more, and more preferably 5 to 10 µm. In addition, a nonwoven fabric which is a mixture containing another fiber thicker than the aforementioned fiber may also be used. If the fiber of 0.5 to 4 µm is used, the lymphocytes can be suitably removed. Furthermore, if the fiber less than 0.5 µm is used, it is possible to enhance the removal efficiency of the physiologically active substance.

The diameter shown here is applied not only to those having the cylindrical shape but also those having a elliptical shape, a rectangular shape or a polygonal shape. An area of a figure obtained by connecting outmost points is calculated, and the diameter of a circle corresponding to the area is calculated. Taking a star shape having five protrudes as an example, the figure obtained by connecting those five apexes is considered. The area thereof is calculated, and the diameter of the circle corresponding to the area is regarded as the diameter of the present invention.

Preferable embodiments of such a nonwoven fabric of the present invention may include those in a form of nonwoven fabric among the aforementioned absorbents and the absorbents for the cancer therapy, which absorb the granulocytes, the monocytes and the cytokine.

In the present invention, the aforementioned nonwoven fabric may constitute a laminate structure combined with the net. The laminate structure may be the bilayer structure of the nonwoven fabric and the net. More preferably, the laminate structure may be a sandwich structure (three layer structure) of the nonwoven fabric-net-nonwoven fabric, obtained by sandwiching the net with the nonwoven fabrics. Of course, it is possible to make a laminate having more layers provided that the bulk density as will described later is considered so as not to give effect on the pressure loss.

As the materials of the net in the present invention, publicly known polymers such as polyamide, polyester, polyacrylonitrile based polymers, polyethylene and polypropylene can be used. As will be described later, when the nonwoven fabric is integrated with the net and then subjected to an organic synthesis reaction for introducing the functional group, the material may be appropriately selected depending on the type of the solvent and a reaction temperature. Polypropylene is particularly preferable in terms of biocompatibility.

When the net structure is formed of multifilaments obtained by combining multiple fibers or spun yarns, the increase of the pressure loss is concerned because media such as blood to be processed pass between the fibers of the multifilaments. Thus it is preferable that the net is formed of a monofilament. When the net is formed of the monofilament, mechanical strength per fiber is easily kept.

The constitution of the net is not particularly limited, and a knotted net, a non-knotted net or a raschel net may be used. Among them, those in which portions where components, e.g., the monofilaments which compose the net are crossed are joined may be suitably used. By the use of such a net, it is possible to obtain the absorbent carrier where there is no movement of the components such as monofilaments as well as the configuration stability and handling property are enhanced when compared with the net not having such a joining. In the net, the composing monofilaments may be joined one another. As a method of joining, knotting and adhesion by heat are available. The adhesion by heat is preferable because a thickness is easily controlled and this method can be performed inexpensively. The shape of a void (mesh) of the net is not particularly limited, and a variety of shape such as a quadrangle such as a rectangle, a lozenge and a hexagonal shape may be employed. Among them, the quadrangle, particularly the rectangle is preferable because the strength when the nonwoven fabrics are laminated, and the handling property are enhanced. Furthermore, the strength when the nonwoven fabrics are laminated, and the handling property are enhanced by disposing the component of the net in a direction having 90±10° against a major or minor axis direction of the nonwoven fabric when the void shape of the net is the quadrangle.

The diameter of the monofilaments which compose the net is preferably 50 μm or more and 1 mm or less, and the thickness of the net is preferably 50 μm or more and 1.2 mm or less. Although the diameter may be larger, such a large diameter is not preferable because a quantity of the absorbent itself per unit volume is reduced thereby.

By using the net, the configuration stability can be imparted to the nonwoven fabric. Thus, even if the bulk density is low, the absorbent carrier having the stable configuration can be produced. It is desirable that openings of the net is as large as possible because the net itself affects the pressure loss. Thus, it is desirable to have 10 mm$^2$ or more void rate per 100 mm$^2$. Particularly preferably, if the net has the openings of about 3 mm square, the configuration stability become good, and the net can be suitably used.

Although the thickness of the absorbent is not particularly limited, in terms of handling, the thickness is preferably 0.1 mm or more and 10 cm or less. For example, when the absorbent is incorporated in a module of a radial flow type such as "Toraymyxin" (registered trade name) supplied from Toray Industries, Inc., the thickness is preferably 1 cm or less because the absorbent is wrapped around a center pipe. These are determined according to the handling method.

The bulk density of the absorbent having the bilayer structure of the net and the nonwoven fabric in the present invention is preferably 0.02 to 0.15 g/cm$^3$, and more preferably 0.05 to 0.15 g/cm$^3$. When the bulk density is increased, the capacity to filtrate the large substances such as leukocytes and cells is enhanced, whereas when it is too large, the clogging easily occurs upon blood circulation. Thus the aforementioned range is preferable. Those having the bulk density of more than 0.15 g/cm$^3$ may be capable of keeping the configuration stability even the nonwoven fabric alone without taking the constitution of the present invention, i.e., the laminate structure of the net and the nonwoven fabric. However, of course, the bulk density of more than 0.15 g/cm$^3$ may be employed in the present invention. The bulk density can be measured, for example, as follows. The absorbent is cut into a square piece having sides of 3 cm. A polypropylene plate having the thickness of 1 mm is put on the piece. The thickness of the absorbent is measured five times, and their mean value is calculated as the thickness. The bulk density is calculated by dividing the weight of this piece by its volume. This measurement is performed for five samples, and the mean value is calculated as the bulk density.

As described above, when the nonwoven fabric is used in the present invention, the leukocytes and the cancer cells can be primarily removed by absorption and filtration with the nonwoven fabric portion. Furthermore it is possible to absorb and remove the physiologically active substance such as cytokine together with the leukocytes and the cancer cells by appropriately selecting the material and the fiber diameter of the nonwoven fabric portion. In order to efficiently absorb and remove the physiologically active substance such as cytokine together with the leukocytes and the cancer cells, it is preferable to introduce and immobilize the particular functional group on the absorbent carrier. By appropriately selecting the material which composes the absorbent carrier, particularly the material which composes the nonwoven fabric portion, it is possible to give an ability to absorb and remove the physiologically active substance such as cytokine without introducing the particular functional group. However, more efficient absorption of the physiologically active substance can be achieved by introducing the functional group.

The fiber which composes the nonwoven fabric is particularly preferably made from a multiple core sea-island type composite fiber in which the core may be polypropylene and the sheath may be polystyrene. Although any combination of the materials may be employed as long as a yarn-making property is good, use of polystyrene as the sheath is particularly preferable because the functional group is easily introduced to the sheath structure. In this case, the functional group having the amino group can be simply introduced by applying an amide methylation method. Conventionally, cyclic peptides (polymyxin B, polymyxin S), polyethyleneimine and quaternary ammonium salts have been introduced. As their specific examples, cyclic peptide residues having an amino group, polyalkyleneimine residues, benzylamino groups, primary, secondary and tertiary alkylamino groups can be used. Among them, the cyclic peptide residues having the amino group and the polyalkyleneimine residues are preferable, and the cyclic peptide residues having the amino group are more preferable because of high absorption performance for the physiologically active substance.

More specifically, the cyclic peptide having the amino group may be the cyclic peptide composed of 2 to 50, preferably 4 to 16 amino acid residues and having one or more amino groups in its side chain, although not limited thereto. As its specific example, polymyxin B, polymyxin E, colistin, gramicidin S, or alkyl derivatives thereof or acyl derivative thereof can be used.

The polyalkyleneimine residue referred to in the present invention means polyalkyleneimine typified by polyethyleneimine, polyhexamethyleneimine and poly (ethyleneimine/decamethyleneimine) copolymer, those obtained by alkylating a part of nitrogen atoms thereof with halogenated hydrocarbon typified by n-hexyl bromide, n-decanyl bromide and n-stearyl bromide or a mixture thereof, or those obtained by acylating the polyalkyleneimine with a fatty acid such as butyric acid, valeic acid, lauryl acid, myristic acid, lenoleic acid and stearic acid.

As the method for producing the absorbent having the bilayer structure of the net and the nonwoven fabric of the present invention, the method for making the laminate structure from the nonwoven fabric and the net previously made separately using a publicly known web adhesion method such as a thermal bond method, a calendar method or a needle punch method is available. As another method, the method for making the absorbent carrier having a sandwich layer structure of the nonwoven fabric-net-nonwoven fabric by previously making a flocculate given pre-punching and sandwiching the net therewith followed by being punched is also available. This method is simpler and preferable. It is possible to stack the pre-punched flocculate on one side of the net.

The extracorporeal circulation column of the present invention may be produced by filling the absorbent (absorbent carrier) having the bilayer structure of the net and the nonwoven fabric in a container, particularly preferably a cylindrical container. As the constitution of the column, preferable are a column in which the absorbent carrier configured in a form of the flat plates are filled in a stacked manner to form a multiple layers; a column in which a cylindrical filter composed of the absorbent carrier rolled up around a core material or without any core material is housed in the cylindrical container having the blood inlet and the blood outlet at both ends; and a column in which a hollow cylindrical filter composed of the absorbent carrier rolled up into the cylindrical shape with both ends sealed is housed in a cylindrical container having a blood inlet and a blood outlet, the blood outlet of the container being provided at the site leading to the outer circumference of the hollow cylindrical filter and the blood outlet of the container being provided at the site leading to the inner circumference of the hollow cylindrical filter. Among them, the column having the hollow cylindrical filter is the most preferable because of efficient removal of the inflammatory leukocytes since most of inflammatory leukocytes in blood are rapidly removed by the nonwoven fabric having a large area on the outer circumference of the cylindrical filter, and remaining few leukocytes coming to the inner circumference of the cylindrical filter and are thoroughly removed by the nonwoven fabric having a small area. For example, upon preparing the cylindrical hollow filter, the nonwoven fabric having the sandwich structure may be prepared so that a longitudinal direction of the net monofilament is perpendicular to each cross section of the nonwoven fabric, whereby a high tensile strength can easily be given to the nonwoven fabric. Having such a constitution, it is possible to improve the handling property upon rolling up the nonwoven fabric around the core material.

The absorbents of the present invention described above may be utilized as the blood processing columns such as extracorporeal circulation columns. When utilized as the extracorporeal circulation column, depending on the amount of the absorbent filled in the column container and a circulation speed of blood, the extracorporeal circulation from the living body is typically performed for one to two hours. 150 to 180 hours after the onset of the extracorporeal circulation, it is thereby possible to realize elevation in the number of lymphocytes, and reduction in the number of granulocytes compared with those before the extracorporeal circulation. Thus, the absorbent and the blood processing column of the present invention are useful for the leukapheresis therapy and the immunostimulatory therapy.

EXAMPLES

The present invention will be more specifically described with reference to the following Experimental Examples.

Example 1 and Comparative Example 1

Measurement of Zeta Potential

A surface zeta potential was calculated on the basis of measurements of a flow potential, a pressure added to run a liquid, and a specific conductivity of the liquid using a flow potential measurement apparatus (ZP-10B supplied from Shimadzu Corporation). As a flowing liquid, an aqueous solution of 1 mM KCl was used, and the measurement was performed at pH 6±1 at temperature of 20±5° C.

(Evaluation of Cytokine Absorbability)

Human natural IL-1 and IL-6 were added to fetal calf serum at 500 pg/mL each. An absorbent was added to this serum solution, which was then shaken at 37° C. for 2 hours, and a supernatant was collected as a sample. The solid/liquid ratio was set to carrier:serum=30 mg:1 mL. Amounts of the cytokine before and after the shaking were measured to obtain the removal rate.

Production Example 1

Nonwoven Fabric

A sea-island composite fiber with 36 island components in which each island component was further composed of a core-sheath composite was obtained under yarn-making conditions of a fiber spinning speed at 800 m/minute and a draw ratio of 3 times, with the following components:

Core component in island component: polypropylene
Sheath component in island component: 90% by weight polystyrene, 10% by weight polypropylene
Sea component: Copolymer polyester containing an ethylene terephthalate unit as a major repeating unit and 3% by weight 5-sodium sulfoisophthalate as a copolymerization component
Composite ratio (weight ratio), Core:Sheath:Sea=44:44:12

A sheet composed of 85% by weight of this fiber and 15% by weight of polypropylene having a diameter of 20 μm was prepared, and the sheet was needle punched to obtain a nonwoven fabric. This nonwoven fabric was treated with an aqueous solution of sodium hydroxide at 90° C. to dissolve the sea component copolymer polyester containing the ethylene terephthalate unit as the major repeating unit and 3% by weight 5-sodium sulfoisophthalate as the copolymerization component. As a result, a nonwoven fabric of a core-sheath fiber with the diameter of 5 μm, having a bulk density of 0.05 g/cm$^3$ (weight per unit area: 250 g/m$^2$) (nonwoven fabric 1) was obtained.

(Intermediate)

Subsequently, 3 g of paraformaldehyde was dissolved in a mixed solution of 600 mL of nitrobenzene and 390 mL of sulfuric acid at 20° C. The mixture was then cooled to 0° C., and 75.9 g of N-methylol-α-chloroacetamide was added thereto and dissolved at 5° C. or below. 5 g of the aforementioned nonwoven fabric 1 was immersed therein and left stand at room temperature for 2 hours. Subsequently, the fiber was taken out, and placed in extremely excessive amount of cold methanol to wash. The fiber was washed thoroughly with methanol, then water, and dried to yield 7.0 g of α-chloroacetamide methylated polystyrene fiber (intermediate A1). The zeta potential thereof was −21 mV.

(Absorbent (Absorbent Material, Absorbent Carrier))

50 g of N,N-dimethyloctylamine and 8 g of potassium iodide were dissolved in 360 mL of DMF to prepare a solution. 5 g of the intermediate A1 was immersed therein, and heated in a bath at 85° C. for 3 hours. The fiber was washed with isopropanol, and then immersed in brine at 1 mol/L. The fiber was subsequently washed with water, and dried in vacuum to yield 8.3 g of dimethyloctyl ammoniumized fiber (absorbent A1). The zeta potential thereof was −1 mV.

50 g of N,N-dimethylhexylamine and 8 g of potassium iodide were dissolved in 360 mL of DMF to prepare a solution. 5 g of the intermediate A1 was immersed therein, and heated in the bath at 85° C. for 3 hours. The fiber was washed with isopropanol, and then immersed in brine at 1 mol/L. The fiber was subsequently washed with water, and dried in vacuum to yield 9.3 g of dimethyllauryl ammoniumized fiber (absorbent A2). The zeta potential thereof was 1.2 mV.

Example 1

50 mL of blood was collected with heparin from a healthy volunteer. Human natural IL-1 and IL-6 were dissolved therein at 500 pg/mL, and the following examination was performed.

150 mg of the absorbent A1 and the absorbent A2 were each filled in a column having an internal volume of 2 mL. 25 mL of the aforementioned blood was circulated at 37° C. for one hour. Then the composition of blood cells was examined using an automatic hemocytometer. IL-1 and IL-6 were quantified by EIA. An absorption rate was calculated from the difference between before and after the circulation. With the absorbent A1, the absorption rates were 19.5% for lymphocytes, 78% for granulocytes and 85% for monocytes, and the absorption rates for IL-1 and IL-6 were 37% and 32%, respectively. Plasma with citric acid prepared using blood from a healthy volunteer was also treated in the same manner, and decrease in activity of coagulation factor XIII was examined (the measurement by synthetic substrate method was entrusted to SRL, Inc. The measurement of coagulation factor XIII described below was also entrusted), which was found out to be 12%. With the absorbent A2, the absorption rates were 21% for lymphocytes, 75% for granulocytes and 83% for monocytes, and the absorption rates for IL-1 and IL-6 were 37% and 40%, respectively. Plasma with citric acid prepared using blood from a healthy volunteer was treated in the same manner, and decrease in activity of coagulation factor XIII was examined, which was found out to be 16%.

Separately, cytokine absorbability was also evaluated. As a result, with the absorbent A1, the absorption rates for IL-1 and IL-6 were 56% and 88%, respectively. With the absorbent A2, the absorption rates for IL-1 and IL-6 were 74% and 93%, respectively.

Comparative Example 1

Using the intermediate A1, the same study as in Example 1 was performed (blood: 25 mL). The absorption rates were 19.5% for lymphocytes, 78% for granulocytes and 78% for monocytes, and the absorption rates for IL-1 and IL-6 were 2% and 3%, respectively.

Plasma with citric acid prepared using blood from a healthy volunteer was treated in the same manner, and decrease in activity of coagulation factor XIII was examined, which was found out to be 16%. Separately, cytokine absorbability was also evaluated. As a result, the absorption rates for IL-1 and IL-6 were 12% and 13%, respectively.

As is evident from the results in the aforementioned Example 1 and Comparative Example 1, the absorbent of the present invention having the zeta potential of −20 mV or more can absorb the granulocytes and the monocytes in blood with high efficiency, and further can simultaneously absorb the cytokines with high efficiency.

Examples 2 to 7

In order to examine the correlation between the absorption rates for the granulocytes and monocytes and the fiber diameter, an absorption test was performed by the following procedure using blood (Ht=43%) from a healthy human donor.

(Measurement of Absorption Rates for Granulocytes and Monocytes, and Correlation Thereof with Fiber Diameter)

The fibers composed of polyethylene terephthalate each having the fiber diameter of 2, 3, 4, 6, 10 or 17 μm were prepared by melt-spinning. The fibers were immersed in blood from the healthy human donor at a solid/liquid ratio of 20 mg/mL (batch absorption test), kept at 37° C. and mixed by overturning three times per minute for 5 minutes. Subsequently, the fiber was removed, and the numbers of granulocytes (represented by the number neutrophils), monocytes and lymphocytes in whole blood before and after the immersion were counted using the hemocytometer (XT1800iv) supplied from Sysmex to obtain their absorption rates. The absorption rate (removal rate) for each blood cell is shown in Table 1.

TABLE 1

Average removal rate in 5 minutes

|  | Fiber diameter (μm) | Neutrophils (Av) | Lymphocytes (Av) | Monocytes (Av) |
|---|---|---|---|---|
| Example 2 | 2 | 17.53 | 2.03 | 26.20 |
| Example 3 | 3 | 25.87 | 2.34 | 28.60 |
| Example 4 | 4 | 33.03 | 2.57 | 44.01 |
| Example 5 | 6 | 25.13 | 1.55 | 38.39 |
| Example 6 | 10 | 32.52 | 4.48 | 53.05 |
| Example 7 | 17 | 6.05 | −0.45 | 12.76 |

(Discussion about Correlation Between Absorption Rate and Fiber Diameter)

In order to examine the correlation between the absorption rates for the granulocytes and monocytes and the fiber diameter, the batch absorption test was performed as described above using blood (Ht=43%) from a healthy human donor. In this test, the removal rate is obtained as about ½ compared to that in circulation using the column. As a result, as is evident from Table 1, it was found that the absorption rate for the lymphocytes is low and less variable in the range of the fiber diameters examined, and that the removal rate of granulocytes (neutrophils) and monocytes can be kept as high as at 50% or more if the fiber diameter exceeds about 3 μm.

Examples 8 to 10 and Comparative Examples 2 to 4

In the following Examples, a relation between the zeta potential and the absorption capacity for lipopolysaccharide, and an effect of facilitating interferon-γ production were examined.

(Measurement of Zeta Potential)

The surface zeta potential was measured under the same condition as in the aforementioned Example 1.

(Evaluation of Cytokine Absorption)

For the evaluation of the cytokine absorption, human natural IL-1 and IL-6 were added to the fetal calf serum at 500 pg/mL each. An absorbent carrier was added to this serum solution, shaken at 37° C. for 2 hours, and the supernatant was collected as a sample. The solid/liquid ratio was set to carrier:serum=30 mg:1 mL. Amounts of the cytokine before and after the shaking were measured to obtain the removal rate. The quantification was performed by EIA using a commercially available kits (IL-1: human IL-1β ELISA kit supplied from R & D System; IL-6: supplied from Kamakura Techno Science).

(Evaluation of Interferon-γ Production)

A cylindrical column made of polypropylene and having the internal volume of 2 mL was filled with 0.3 g of the absorbent, and 10 mL of blood from a human volunteer was passed therethrough at a flow rate of 2 mL/minute to yield blood stimulated with the absorbent. Lymphocyte fractions were separated from blood which has or has not passed through the column by Ficoll density gradient centrifugation. Lymphocyte-enriched solutions made of blood before the contact with the absorbent and of blood 8 hours after the contact were stimulated with 1 to 10 μg of PHA (phytohemagglutinin-L supplied from Wako Pure Chemical Industries Ltd.), and concentrations of interferon-γ before and after the stimulation were measured. The quantification was performed by EIA using the commercially available kit (human interferon-γ ELISA kit supplied from ENDOGEN). A value of (interferon-γ concentration after stimulation)/(interferon-γ concentration before stimulation) was calculated to use as an interferon-γ production activity.

(Measurement of Blood Cell Numbers)

The blood cell numbers and a hematocrit value in body fluid were measured using XT-1800iv supplied from Sysmex.

(Measurement of LPS)

The amount of LPS absorption was measured using a toxinometer supplied from Wako Pure Chemical Industries Ltd. LPS (catalogue No. 120-04531) supplied from Wako Pure Chemical Industries Ltd. was dispersed at 10 ng/mL in saline containing 1% by volume FCS, and incubated with 300 mg of the absorbent in a water bath at 37° C. for 4 hours. The amount of remaining LPS in the supernatant was measured using the toxinometer. The removed amount and the removal rate of LPS were obtained as a difference and a ratio between the measured amount and the amount of the LPS in the LPS-added solution. The criteria for the LPS absorption capacity are 90% or more removal rate and 100 pg/mL or more absorption amount.

Production Example 2

Nonwoven Fabric

A sea-island composite fiber with 36 island components in which each island component was further composed of a core-sheath composite was obtained under yarn-making conditions of a fiber spinning speed at 800 m/minute and a draw ratio of 3 times, with the following components:

Core component in island component: polypropylene

Sheath component in island component: 90% by weight polystyrene, 10% by weight polypropylene Sea component: Copolymer polyester containing an ethylene terephthalate unit as a major repeating unit and 3% by weight 5-sodium sulfoisophthalate as a copolymerization component Composite ratio (weight ratio), Core:Sheath:Sea=44:44:12

A sheet composed of 75% by weight of this fiber and 25% by weight of polypropylene having a diameter of 20 µm was prepared, and the sheet was needle punched to obtain a nonwoven fabric. This nonwoven fabric was treated with an aqueous solution of sodium hydroxide at 90° C. to dissolve the sea component copolymer polyester containing the ethylene terephthalate unit as the major repeating unit and 3% by weight 5-sodium sulfoisophthalate as the copolymerization component. As a result, a nonwoven fabric of a core-sheath fiber with the diameter of 4.5 µm, having a bulk density of 0.03 g/cm$^3$ (weight per unit area: 200 g/m$^2$) (nonwoven fabric 2) was obtained.

(Intermediate)

Subsequently, 3 g of paraformaldehyde was dissolved in a mixed solution of 600 mL of nitrobenzene and 390 mL of sulfuric acid at 20° C. The mixture was then cooled to 0° C., and 75.9 g of N-methylol-α-chloroacetamide was added thereto and dissolved at 5° C. or below. Immediately after the temperature of the mixture was elevated to 20° C., 5 g of the aforementioned nonwoven fabric 2 was immersed therein and left stand at room temperature for 2 hours. Subsequently, the fiber was taken out, and placed in extremely excessive amount of cold methanol to wash. The fiber was washed thoroughly with methanol, then water, and dried to yield 7.0 g of α-chloroacetamide methylated polystyrene fiber (intermediate A2). The zeta potential thereof was −23 mV.

(Absorbents)

50 g of N,N-dimethyloctylamine and 8 g of potassium iodide were dissolved in 360 mL of methanol to prepare a solution. 5 g of the intermediate A2 was immersed therein, and heated in a bath at 50° C. for 3 hours. The fiber was washed with isopropanol, and then immersed in brine at 1 mol/L. The fiber was subsequently washed with water, and dried in vacuum to yield 8.1 g of dimethyloctyl ammoniumized fiber (absorbent A3). The zeta potential thereof was −0.3 mV.

50 g of N,N-dimethylhexylamine and 8 g of potassium iodide were dissolved in 360 mL of methanol to prepare a solution. 5 g of the intermediate A3 was immersed therein, and heated in the bath at 50° C. for 3 hours. The fiber was washed with isopropanol, and then immersed in brine at 1 mol/L. The fiber was subsequently washed with water, and dried in vacuum to yield 7.3 g of dimethylhexyl ammoniumized fiber (absorbent A4). The zeta potential thereof was 2.2 mV.

Example 8

50 mL of blood was collected with heparin from a healthy volunteer. Human natural IL-1 and IL-6 were dissolved therein at 500 pg/mL, and the following examination was performed.

150 mg of the absorbent A3 and the absorbent A4 were each filled in a column having an internal volume of 2 mL. 25 mL of the aforementioned blood was circulated at 37° C. for one hour. Then the composition of blood cells was examined using an automatic hemocytometer (XT1800iv supplied from Sysmex). IL-1 and IL-6 were quantified by EIA. With the absorbent A3, the reduction rates were 14.5% for lymphocytes, 72% for granulocytes and 82% for monocytes, and the reduction rates for IL-1 and IL-6 were 33% and 52%, respectively. With the absorbent A4, the reduction rates were 21% for lymphocytes, 75% for granulocytes and 83% for monocytes, and the reduction rates for IL-1 and IL-6 were 37% and 40%, respectively.

The removal rates for LPS were 98% and 97% with the absorbents A3 and A4, respectively.

Separately, cytokine absorption was evaluated. As a result, the removal rates with the absorbent A3 were 56% and 88% for IL-1 and Il-6, respectively. The removal rates with the absorbent A4 were 74% and 93% for IL-1 and Il-6, respectively.

Example 9

Extracorporeal Circulation Therapy 0.3 g of the absorbent A3 was filled in a cylindrical column made of polypropylene and having an internal diameter of 1 cm and the internal volume of 2 mL, to prepare an extracorporeal circulation column. WKAH:Hkm rat (male) at the age of 12 weeks was subcutaneously inoculated at its back with 1×10$^6$ cells of 4-dimethylaminoazobenzene-induced hepatic cancer cells KDH-8 (Satoshi Yano, *Hokkaido Ishi* (Hokkaido Journal of Medical Science) Vol. 68 No. 5: 654-664, 1993). The cancer cells settled at a probability of 100% (typically the tumor starts to grow one week after the inoculation, and the tumor-bearing rat dies 5.5 weeks after the inoculation.). The extracorporeal circulation column was preliminarily washed with saline containing 1000 units of sodium heparin, and was further washed with 500 mL of saline before the extracorporeal circulation.

The extracorporeal circulation therapy was given to the rat 2 weeks after inoculating the KDH cells. Blood was collected from femoral vein, and the numbers of granulocytes and lymphocytes before the extracorporeal circulation were counted using the automatic hemocytometer. As a result, the number of granulocytes was 9300 cells/µL and the number of lymphocytes was 8100 cells/µL. A circuit in which blood is passed through the extracorporeal circulation column and then returned to the femoral vein was constituted, and the extracorporeal circulation was performed at a flow rate of 2 mL/minute for one hour. During the extracorporeal circulation, an injection solution of sodium heparin (supplied from Ajinomoto Co., Inc.) was continuously injected at a speed of 200 U/hour. The extracorporeal circulation column was preliminarily washed with saline containing 1000 units of sodium heparin, and was further washed with 500 mL of saline before the extracorporeal circulation. After performing the extracorporeal circulation, procedures such as suture were given. After the lapse of 160 hours, blood was collected and the numbers of granulocytes and lymphocytes were counted using the automatic hemocytometer. As a result, the numbers of granulocytes and lymphocytes were 6700 cells/µL and 11400 cells/µL, respectively, and the number of lymphocytes increased whereas the number of granulocytes decreased compared with those before the extracorporeal circulation. After this rat was bled for additional 3 weeks, the extracorporeal circulation was performed again in the same manner as the above. The numbers of granulocytes and lymphocytes before the extracorporeal circulation were counted using the automatic hemocytometer. The numbers of granulocytes and lymphocytes were 28000 cells/µL and 7400 cells/µL, respectively. Blood was collected 160 hours after the extracorporeal circulation, and the numbers of granulocytes and lymphocytes were counted using the automatic hemocytometer. As a result, the numbers of granulocytes and lymphocytes were 26700 cells/µL and 8400 cells/µL, respectively. Thus the number of lymphocytes increased whereas the number of granulocytes decreased compared with those before the extracorporeal circulation.

Comparative Example 2

Using the intermediate A2, the same study as in Example 8 (blood: 25 mL) was performed. As a result, the numbers of lymphocytes, granulocytes and monocytes decreased by 19.5%, 78% and 78%, respectively. IL-1 and IL-6 decreased by 2% and 3%, respectively. The removal rate for LPS was 78%. Separately, cytokine absorption was evaluated. As a result, the removal rates were 12% and 13% for IL-1 and IL-6, respectively.

Comparative Example 3

0.3 g of the intermediate A2 was filled in the cylindrical column made of polypropylene and having the internal diameter of 1 cm and the internal volume of 2 mL, and the extracorporeal circulation therapy was given to the rat 2 weeks after inoculating the KDH cells in the same manner as in Example 8. Blood was collected from the femoral vein, and the numbers of granulocytes and lymphocytes before the extracorporeal circulation were counted using the automatic hemocytometer. As a result, the number of granulocytes was 10300 cells/µL and the number of lymphocytes was 8400 cells/µL. Procedures such as suture were given. After the lapse of 160 hours, blood was collected and the numbers of granulocytes and lymphocytes were counted using the automatic hemocytometer. As a result, the numbers of granulocytes and lymphocytes were 15200 cells/µL and 8100 cells/µL, respectively Thus the number of lymphocytes decreased whereas the number of granulocytes increased compared with those before the extracorporeal circulation.

Example 10

A capacity to produce interferon-γ was evaluated using human peripheral blood and the absorbent A4. When not treated with the absorbent, a concentration ratio of interferon-γ was 20.4 times. On the contrary, when treated with the absorbent, the concentration ratio of interferon-γ was 35.2 times, showing that the immunoreactivity was enhanced.

Comparative Example 4

The capacity to produce interferon-γ was evaluated using human peripheral blood and the intermediate A2. When not treated with the absorbent, the concentration ratio of interferon-γ was 20.1 times, whereas, when treated with the absorbent, the concentration ratio of interferon-γ was 21.2 times, showing that the immunoreactivity was not changed.

Example 11

Production Example 3

Nonwoven Fabric

A sea-island composite fiber with 36 island components in which each island component was further composed of a core-sheath composite was obtained under yarn-making conditions of a fiber spinning speed at 800 m/minute and a draw ratio of 3 times, with the following components:
Core component in island component: polypropylene
Sheath component in island component: 90% by weight polystyrene, 10% by weight polypropylene
Sea component: Copolymer polyester containing an ethylene terephthalate unit as a major repeating unit and 3% by weight 5-sodium sulfoisophthalate as a copolymerization component
Composite ratio (weight ratio), Core:Sheath:Sea=44:44:12
A sheet composed of 50% by weight of this fiber and 50% by weight of polypropylene having a diameter of 20 µm was prepared, and the sheet was needle punched to obtain a nonwoven fabric. This nonwoven fabric was treated with an aqueous solution of sodium hydroxide at 90° C. to dissolve the sea component copolymer polyester containing the ethylene terephthalate unit as the major repeating unit and 3% by weight 5-sodium sulfoisophthalate as the copolymerization component. As a result, a nonwoven fabric of a core-sheath fiber with the diameter of 4.5 µm, having a bulk density of 0.03 g/cm$^3$ (weight per unit area: 200 g/m$^2$) (nonwoven fabric A3) was obtained.
(Intermediate)
Subsequently, 3 g of paraformaldehyde was dissolved in a mixed solution of 600 mL of nitrobenzene and 390 mL of sulfuric acid at 20° C. The mixture was then cooled to 0° C., and 75.9 g of N-methylol-α-chloroacetamide was added thereto and dissolved at 5° C. or below. Immediately after the temperature of the mixture was elevated to 20° C., 5 g of the aforementioned nonwoven fabric 3 was immersed therein and left stand at room temperature for 2 hours. Subsequently, the fiber was taken out, and placed in extremely excessive amount of cold methanol to wash. The fiber was washed thoroughly with methanol, then water, and dried to yield 6.3 g of α-chloroacetamide methylated polystyrene fiber (intermediate A3). The zeta potential thereof was −26 mV.
(Absorbent)
50 g of N,N-dimethyloctylamine and 8 g of potassium iodide were dissolved in 360 mL of methanol to prepare a solution. 5 g of the intermediate A3 was immersed therein, and heated in a bath at 50° C. for 3 hours. The fiber was washed with isopropanol, and then immersed in brine at 1 mol/L. The fiber was subsequently washed with water, and dried in vacuum to yield 6.8 g of dimethyloctyl ammoniumized fiber (absorbent A5). The zeta potential thereof was −12.3 mV.

Example 11

50 mL of blood was collected with heparin from a healthy volunteer. Human natural IL-1 and IL-6 were dissolved therein at 500 pg/mL, and the following examination was performed.

150 mg of the absorbent A5 obtained in the aforementioned Production Example 3 was filled in a column having an internal volume of 2 mL. 25 mL of the aforementioned blood was circulated at 37° C. for one hour. Then the composition of blood cells was examined using an automatic hemocytometer (XT1800iv supplied from Sysmex). IL-1 and IL-6 were quantified by EIA. With the absorbent A5, the reduction rates were 10.5% for lymphocytes, 61% for granulocytes and 67% for monocytes, and the reduction rates for IL-1 and IL-6 were 24% and 38%, respectively.

The LPS removal rate was 90% with the absorbent A5.

Separately, cytokine absorption was evaluated. As a result, the removal rates of the absorbent A5 were 44% and 61%, for IL-1 and IL-6, respectively.

From the results in the aforementioned Examples 8 to 11 and Comparative Examples 2 to 4, it has been demonstrated that the present invention which is the absorbent having the zeta potential of −20 mV or more can absorb the granulocytes and the monocytes in blood with high efficiency, and further that when the zeta potential is −15 mV or more, the absorbent can simultaneously absorb LPS and the cytokine with high efficiency. It has been found that alteration in the numbers of granulocytes and lymphocytes after the extracorporeal circulation is changed toward a proportion thought to be normal although the mechanism therefor is unknown.

Examples 12 to 15 and Comparative Examples 5 to 8

The evaluation methods, the procedures and the conditions for performing each Example were as follows.

1. Analysis of Components in Blood

The concentration of TGF-β was measured using a human TGF-β1 immunoassay kit supplied from Genzyme Techne. The concentration of the immunosuppressive acidic protein was measured using a rat IAP plate supplied from Sanko Junyaku Co., Ltd. The concentration of albumin was measured using Albumin B Test Wako which is an albumin analysis kit.

2. Equilibrium Absorption Capacity of Absorbent for TGF-β

Sera from five tumor-bearing rats were collected to prepare 30 mL of a serum sample from the tumor-bearing rats. 50 mg of the absorbent was placed in 1 mL of this serum sample, which was then shaken at 37° C. for 4 hours. The TGF-β concentration in the supernatant was measured, and the difference between the concentrations before and after the absorption was divided by the absorbent weight (0.05), to obtain the equilibrium absorption capacity for TGF-β.

3. Preparation of Absorbent (Water-Insoluble Polymer)

A sea-island composite fiber with 36 island components in which each island component was further composed of a core-sheath composite was obtained under yarn-making conditions of a fiber spinning speed at 800 m/minute and a draw ratio of 3 times, with the following components:

Core component in island component: polypropylene
Sheath component in island component: 90% by weight polystyrene, 10% by weight polypropylene
Sea component: Copolymer polyester containing an ethylene terephthalate unit as a major repeating unit and 3% by weight 5-sodium sulfoisophthalate as a copolymerization component
Composite ratio (weight ratio), Core:Sheath:Sea=45:45:10

A sheet composed of 85% by weight of this fiber and 15% by weight of polypropylene having a diameter of 17 μm was prepared, and the sheet was needle punched to obtain a nonwoven fabric. This nonwoven fabric was treated with an aqueous solution of sodium hydroxide at 95° C. for two hours to dissolve the sea component copolymer polyester containing the ethylene terephthalate unit as the major repeating unit and 3% by weight 5-sodium sulfoisophthalate as the copolymerization component. As a result, a nonwoven fabric of a core-sheath fiber with the diameter of 5 μm, having a bulk density of 0.07 g/cm$^3$ (weight per unit area: 250 g/m$^2$) was obtained.

(Intermediate)

Subsequently, 3 g of paraformaldehyde was dissolved in a mixed solution of 600 mL of nitrobenzene and 390 mL of sulfuric acid at 20° C. The mixture was then cooled to 0° C., and 75.9 g of N-methylol-α-chloroacetamide was added thereto and dissolved at 5° C. or below. 5 g of the aforementioned nonwoven fabric was immersed therein and left stand at room temperature for 2 hours. Subsequently, the fiber was taken out, and placed in extremely excessive amount of cold methanol to wash. The fiber was washed thoroughly with methanol, then water, and dried to yield 7.0 g of α-chloroacetamide methylated polystyrene fiber (intermediate C1).

(Absorbent)

50 g of N,N-dimethyloctylamine and 8 g of potassium iodide were dissolved in 360 mL of DMF to prepare a solution. 5 g of the intermediate C1 was immersed therein, and heated in a bath at 85° C. for 3 hours. The fiber was washed with isopropanol, and then immersed in brine at 1 mol/L. The fiber was subsequently washed with water, and dried in vacuum to yield 8.3 g of dimethyloctyl ammoniumized fiber (absorbent C1).

50 g of N,N-dimethylhexylamine and 8 g of potassium iodide were dissolved in 360 mL of DMF to prepare a solution. 5 g of the intermediate C1 was immersed therein, and heated in the bath at 85° C. for 3 hours. The fiber was washed with isopropanol, and then immersed in brine at 1 mol/L. The fiber was subsequently washed with water, and dried in vacuum to yield 9.3 g of dimethyllauryl ammoniumized fiber (absorbent C2).

(Sulfonated Fiber: Comparative Fiber)

500 mg of paraformaldehyde was dissolved in 50 mL of sulfuric acid, to prepare a solution. 5 g of the nonwoven fabric 1 was immersed therein, and heated at 95° C. for one hour. The fiber was subsequently washed with water, washed with brine at 1 mol/L, washed with water, and then dried to yield 7.3 g of sulfonated fiber (comparative absorbent C1).

(Preparation of Tumor-Bearing Rats)

WKAH:Hkm rat (male) at the age of 12 weeks was subcutaneously inoculated at its back with 1×10$^6$ cells of 4-dimethylaminoazobenzene-induced hepatic cancer cells KDH-8 (Satoshi Yano, *Hokkaido Ishi* (Hokkaido Journal of Medical Science) Vol. 68 No. 5: 654-664, 1993). The cancer cells settled at a probability of 100% (typically the tumor starts to grow one week after the inoculation, and the tumor-bearing rat dies 5.5 weeks after the inoculation.).

(Production of Extracorporeal Circulation Column)

A cylindrical column made of polypropylene having the internal diameter of 1 cm and the internal volume of 2 mL was filled with either one of the absorbent C1, the absorbent C2, the comparative absorbent C1 and the nonwoven fabric composed of polyethylene terephthalate fiber having the diameter of 25 μm, to prepare an extracorporeal circulation column for cancer therapy. Columns filled with 0.38 g of each absorbent were allotted to Example 12 (absorbent C1), Example 13 (absorbent C2), Comparative Example 5 (comparative absorbent C1), and Comparative Example 6 (polyethylene terephthalate fiber having the diameter of 25 μm). Likewise, columns filled with 0.18 g of each absorbent were allotted to Example 14 (absorbent C1), Example 15 (absorbent C2), Comparative Example 7 (comparative absorbent C1), and Comparative Example 8 (polyethylene terephthalate fiber having the diameter of 25 μm). The zeta potential of the absorbent was −20 mV or more in all of the Examples.

(Preparation of Tumor-Bearing Rats and Extracorporeal Circulation)

The extracorporeal circulation column for the cancer therapy was preliminarily washed with saline containing 1000 units of sodium heparin, and was further washed with 500 mL of saline before the extracorporeal circulation.

Two weeks after inoculating the KDH cells, the extracorporeal circulation was performed at a flow rate of 2 mL/mL for 60 minutes. Blood was collected from the femoral artery, passed through the absorbent column and then returned to the femoral vein. During the extracorporeal circulation, the sodium heparin solution for injection (supplied from Takeda Chemical Industries, Ltd.) was continuously injected at a rate of 100 U/hour.

Blood before and after the extracorporeal circulation was collected from the rat, and the concentration of TGF-β in the serum was measured. Survival days after inoculating the cancer cells were observed. The results in Table 2 were obtained thereby.

(Evaluation of In Vitro Removal of Blood Cells)

25 mL of blood is collected from a healthy volunteer. Immediately after collection, 10 U/mL of heparin is added thereto, and the following circulation is performed within 3 hours. The blood is kept at 37° C., and circulated through the column with a volume of 2 mL (filled with the predetermined amount of the absorbent which has punched out to be configured in a shape having the diameter of 1 cm) at a flow rate of 2 mL/minutes for 90 minutes. After the treatment with the column, leukocytes in blood are fractionated using a blood cell counter, and the removal rates of lymphocytes, granulocytes (neutrophils) and monocytes are calculated. The standard removal rate is set to the value at the time point of 60 minutes.

TABLE 2

|  | Filled amount of absorbent for cancer therapy (g) | Rat body weight (kg) | TGF-β concentration in serum (ng/mL) | Granulocyte removal rate (%) |
| --- | --- | --- | --- | --- |
| Example 12 | 0.38 | 0.31 | 33 | 78 |
| Example 13 | 0.38 | 0.32 | 36 | 68 |
| Example 14 | 0.18 | 0.34 | 35 | 52 |
| Example 15 | 0.18 | 0.31 | 33 | 52 |
| Comparative Example 5 | 0.38 | 0.33 | 33 | 58 |
| Comparative Example 6 | 0.38 | 0.31 | 34 | 21 |
| Comparative Example 7 | 0.18 | 0.37 | 35 | 44 |
| Comparative Example 8 | 0.18 | 0.32 | 36 | 18 |

Blood latent    Survival after

TABLE 2-continued

|  | Monocyte removal rate (%) | Lymphocyte Removal rate (%) | TGF-β removal rate (%) | inoculating cancer cells (weeks) |
| --- | --- | --- | --- | --- |
| Example 12 | 88 | 19 | 61 | 7.3 |
| Example 13 | 84 | 17 | 72 | 8.6 |
| Example 14 | 66 | 12 | 26 | 6.7 |
| Example 15 | 68 | 13 | 39 | 7.3 |
| Comparative Example 5 | 59 | 12 | 3 | 4.3 |
| Comparative Example 6 | 16 | 11 | 6 | 4.7 |
| Comparative Example 7 | 22 | 12 | 3 | 4.3 |
| Comparative Example 8 | 14 | 10 | 3 | 4.3 |

In Examples 12 and 13, the concentrations of TGF-β in blood decreased and the duration of life was extended. In Examples 12 to 15 and Comparative Examples 5 to 8, it has been shown that the concentrations of TGF-β in blood after the extracorporeal circulation is in inverse proportion to the duration of life after inoculating the cancer cells. It has been also shown that the concentrations of TGF-β in blood decrease in proportion to the amount of the absorbent used. In Comparative Examples, the concentrations of TGF-β in blood did not decrease, and the duration of life after inoculating the cancer cells was short. As the duration of life of rats which were not treated was 5.5 weeks, Comparative Examples 5 to 8 demonstrate that, when the extracorporeal circulation is performed using the column having the low absorption capacity for TGF-β, the duration of life is rather shortened.

Examples 16 and 17 and Comparative Examples 9 and 10

Example 16

Absorbent Carrier

A sea-island composite fiber with 36 island components in which each island component was further composed of a core-sheath composite was obtained under yarn-making conditions of a fiber spinning speed at 800 m/minute and a draw ratio of 3 times, with the following components:

Core component in island component: polypropylene

Sheath component in island component: 90% by weight polystyrene, 10% by weight polypropylene Sea component: Copolymer polyester containing an ethylene terephthalate unit as a major repeating unit and 3% by weight 5-sodium sulfoisophthalate as a copolymerization component Composite ratio (weight ratio), Core:Sheath:Sea=42:43:15

A nonwoven fabric composed of 85% by weight of this fiber and 15% by weight of polypropylene having a diameter of 20 μm was prepared, and the sheet was needle punched to obtain a nonwoven fabric. With two sheets of this nonwoven fabric, a polyester net (thickness: 0.4 mm, monofilament diameter: 0.3 mm) having openings of 2 mm square was sandwiched. Setting the sandwiched sheet so that the slope against the cut surface of the nonwoven fabric was 90°, needle punching was performed. This nonwoven fabric was treated with an aqueous solution of sodium hydroxide at 90° C. to dissolve the sea component copolymer polyester containing the ethylene terephthalate unit as the major repeating unit and 3% by weight 5-sodium sulfoisophthalate as the copolymerization component. As a result, an absorbent carrier of a core-sheath fiber with the diameter of 5 μm, having a bulk density of 0.02 g/cm³ (weight per unit area: 150 g/m²) (absorbent carrier B1) was obtained. The absorbent carrier was rolled up at a constant speed, and it was found out that the carrier was able to be rolled up stably. Thus cylindrical filters having an uniform shape were obtained.

(Intermediate)

Subsequently, 3 g of paraformaldehyde was dissolved in a mixed solution of 600 mL of nitrobenzene and 390 mL of sulfuric acid at 20° C. The mixture was then cooled to 0° C., and 75.9 g of N-methylol-α-chloroacetamide was added thereto and dissolved at 5° C. or below. 5 g of the aforementioned absorbent carrier B1 was immersed therein and left stand at room temperature for 2 hours. Subsequently, the fiber was taken out, and placed in extremely excessive amount of cold methanol to wash. The fiber was washed thoroughly with methanol, then water, and dried to yield 7.0 g of α-chloroacetamide methylated polystyrene fiber (intermediate B1).

(Functional Group-Introduced Absorbent (Absorbent Carrier))

50 g of N,N-dimethyloctylamine and 8 g of potassium iodide were dissolved in 360 mL of DMF to prepare a solution. 5 g of the intermediate B1 was immersed therein, and heated in a bath at 85° C. for 3 hours. The fiber was washed with isopropanol, and then immersed in brine at 1 mol/L. The fiber was subsequently washed with water, and dried in vacuum to yield 8.3 g of dimethyloctyl ammoniumized fiber (functional group-introduced absorbent carrier B1).

Separately, 50 g of N,N-dimethyllaurylamine and 8 g of potassium iodide were dissolved in 360 mL of DMF to prepare a solution. 5 g of the aforementioned intermediate By was immersed therein, and heated in a hot bath at 85° C. for 3 hours. The fiber was washed with isopropanol, and then immersed in brine at 1 mol/L. The fiber was subsequently washed with water, and dried in vacuum to yield 9.3 g of dimethyllauryl ammoniumized fiber (functional group-introduced absorbent carrier B2). The functional group-introduced absorbent carriers B1 and B2 contain the net, and thus were undeformable and capable of keeping good shapes.

Comparative Example 9

The nonwoven fabric was prepared in the same manner as in Example 16, except that the needle punching was given to the sea-island composite fiber made in Example 16 without using the net. This nonwoven fabric was treated with an aqueous solution of sodium hydroxide at 90° C. to dissolve the sea component copolymer polyester containing the ethylene terephthalate unit as the major repeating unit and 3% by weight 5-sodium sulfoisophthalate as the copolymerization component. As a result, a nonwoven fabric of a core-sheath fiber with the diameter of 5 μm, having a bulk density of 0.02 g/cm³ (weight per unit area: 150 g/m²) (nonwoven fabric B1) was obtained. This nonwoven fabric had poor strength toward a crosswise direction. This fabric elongated during the synthesis of the intermediate and the absorbent, and was thus unable to keep its bulk density.

Example 17

50 mL of blood was collected with heparin from a healthy volunteer. Human natural IL-6 (referred to hereinbelow as IL-6) was dissolved therein at 500 pg/mL, and the following examination was performed.

150 mg of the absorbent (functional group-introduced absorbent carrier B1) was filled in the column having the internal volume of 2 mL. 25 mL of the aforementioned blood was circulated at 37° C. for one hour. Then the composition of blood cells was examined using the automatic hemocytometer, and IL-6 was quantified by EIA. The numbers of lymphocytes and granulocytes decreased by 12.5% and 67%, respectively. IL-6 also decreased by 35%. In this experiment, the pressure loss did not increase.

Comparative Example 10

The nonwoven fabric prepared in Comparative Example 10 was filled in the column in the same amount in the same manner as in Example 17, and the examination was performed using remaining 25 mL blood.

In this experiment, the pressure loss was increased at 45 minutes, it exceeded 200 mmHg, and thus the examination was discontinued. The numbers of lymphocytes and granulocytes decreased by 31.5% and 69%, respectively, and IL-6 also decreased by 35%.

Example 18

Upon preparing a nonwoven fabric in the same manner as in Example 16, the polyester net (thickness: 0.4 mm, monofilament diameter: 0.3 mm) having openings of 2 mm square was sandwiched with the nonwoven fabric sheets, and the sandwiched sheet was set so that the slope was 110 degrees against the cut surface of the nonwoven fabric. When rolled up at a constant speed, the elongation of the nonwoven fabric was confirmed and rolling up tension was not stabilized. The thickness of the nonwoven fabric was not constant, and cylindrical filters having an uniform shape were not obtainable.

150 mg of this nonwoven fabric was filled in the column having the internal volume of 2 mL. 25 mL of the aforementioned blood was circulated at 37° C. for one hour, and then the composition of blood cells was examined using the automatic hemocytometer. IL-6 was also quantified by EIA. As a result, the numbers of lymphocytes and granulocytes decreased by 12.5% and 67%, respectively. IL-6 also decreased by 35%. In this experiment, the pressure loss did not increase.

INDUSTRIAL APPLICABILITY

According to the present invention, there is provided an absorbent capable of absorbing and removing from blood the leukocytes and the inflammatory and immunosuppressive cytokines, with low removal rate for useful components in blood. Such an absorbent of the present invention can be provided for a variety of uses such as leukapheresis therapy, immunostimulatory therapy and cancer therapy.

This material is suitably applicable to a column for affinity chromatography and a blood column for treatment, particularly an extracorporeal circulation column, in a form of molded articles such as a petri dish, a bottle, a membrane, a fiber, a hollow fiber, a granular matter or an assembly thereof.

The invention claimed is:

1. An absorbent having a zeta potential of −20 mV or more and having an ability to absorb granulocytes, monocytes and cytokine in blood,
   wherein said absorbent comprises a water-insoluble carrier having a functional group bound thereto,
   wherein the shape of said water-insoluble carrier is selected from the group consisting of a fiber or a hollow fiber having a fiber diameter of more than 3 μm, and a bead with a protrusion having a diameter of more than 3 μm on its surface, wherein an absorption rate for lymphocytes is 40% or less, wherein said water-insoluble carrier comprises a water-insoluble polymer having a quaternary ammonium salt and/or a straight amino group bound to a linking group selected from the group consisting of an alkyl group, an acetyl group, and an acetamidemethyl group, the quaternary ammonium salt being a group obtained by immobilizing at least one amine selected from the group consisting of N,N-dimethylhexylamine, N,N-dimethyloctylamine, and N,N-dimethyllaurylamine, and said straight amino group being obtained by immobilizing tetraethylenepentamine, and wherein a density of the quaternary ammonium salt and/or the straight amino group in said water-insoluble carrier is 0.01 to 2.0 mol per 1 mol of a repeating unit of said water-insoluble polymer.

2. The absorbent according to claim 1 wherein said cytokine is at least one selected from the group consisting of interleukin-1 (XL-1), interleukin-6 (IL-6), interleukin-8 (IL-8), interleukin-10 (IL-10), TNF-α, transforming growth factor-beta (TGF-β), vascular endothelial growth factor (VEGF) and immunosuppressive acidic protein (IAP).

3. The absorbent according to claim 1 wherein the absorption rate for coagulation factor XIII is 30% or less.

4. The absorbent according to claim 1 having the zeta potential of −15 mV or more and having a capacity to absorb 90% or more lipopolysaccharide (LPS) in saline containing 1% by volume fetal calf serum (FCS).

5. The absorbent according to claim 1 wherein the shape of said water-insoluble carrier is selected from the group consisting of a fiber or a hollow filament having a fiber diameter of 4 to 8 μm, and a bead with a protrusion having a diameter of 4 to 8 μm on its surface.

6. The absorbent according to claim 5 wherein the shape of said water-insoluble carrier is selected from the group consisting of a fiber or a hollow filament having a fiber diameter of 4.5 to 8 μm, and a bead with a protrusion having a diameter of 4.5 to a μm on its surface.

7. The absorbent according to claim 1 wherein said water-insoluble carrier further comprises a fiber or a hollow filament having a fiber diameter of 10 to 50 μm.

8. The absorbent according to claim 1 wherein the absorption rate for granulocytes is 50% or more and the absorption rate for monocytes is 50% or more.

9. The absorbent according to claim 1 for use in leukapheresis therapy or immunostimulatory therapy.

10. A blood processing column comprising a container and the absorbent according to claim 1 filled therein.

11. A blood processing column comprising a cylindrical container and the absorbent according to claim 1 filled therein.

12. The blood processing column according to claim 10 for use in blood circulation.

13. The blood processing column according to claim 10 wherein an extracorporeal circulation therethrough with a living body results in increase in a number of lymphocytes and decrease in a number of granulocytes, said numbers being measured 150 to 180 hours after finishing the extracorporeal circulation and compared with those before the extracorporeal circulation.

14. The blood processing column according to claim 11 for use in blood circulation.

15. The blood processing column according to claim 11 wherein an extracorporeal circulation therethrough with a living body results in increase in a number of lymphocytes and decrease in a number of granulocytes, said numbers being measured 150 to 180 hours after finishing the extracorporeal circulation and compared with those before the extracorporeal circulation.

16. The absorbent according to claim 1 wherein said insoluble carrier comprises polyethylene, polypropylene, polystyrene or a combination thereof.

17. An absorbent having a zeta potential of −15 mV or more and having an ability to absorb granulocytes, monocytes and cytokine in blood; having an absorption rate for coagulation factor XIII of 30% or less; and having a capacity to absorb 90% or more lipopolysaccharide (LPS) in saline containing 1% by volume fetal calf serum (FCS);

wherein said absorbent comprises a water-insoluble carrier having a functional group bound thereto, wherein said water-insoluble carrier comprises a fiber or a hollow filament having a fiber diameter of 10 to 50 μm, wherein an absorption rate for lymphocytes is 40% or less, wherein said water-insoluble carrier comprises a water-insoluble polymer having a quaternary ammonium salt and/or a straight amino group bound to a linking group selected from the group consisting of an alkyl group, an acetyl group, and an acetamidemethyl group, the quaternary ammonium salt being a group obtained by immobilizing at least one amine selected from the group consisting of N,N-dimethylhexylamine, N,N-dimethyloctylamine, and N,N-dimethyllaurylamine, and said straight amino group being obtained by immobilizing tetraethylenepentamine, and wherein a density of the quaternary ammonium salt and/or the straight amino group in said water-insoluble carrier is 0.01 to 2.0 mol per 1 mol of a repeating unit of said water-insoluble polymer.

* * * * *